(12) United States Patent
Ishiwata et al.

(10) Patent No.: US 6,828,428 B2
(45) Date of Patent: Dec. 7, 2004

(54) IGA NEPHROPATHY-RELATED GENES

(75) Inventors: Tetsuyoshi Ishiwata, Tokyo (JP);
Mikiko Sakurada, SanDiego, CA (US);
Ayako Nishimura, Tokyo (JP); Satoshi Nakagawa, Tokyo (JP); Tatsunari Nishi, Tokyo (JP); Tetsuro Kuga, Tokyo (JP); Shigemasa Sawada, Tokyo (JP); Masami Takei, Saitama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/090,672

(22) Filed: Jun. 4, 1998

(65) Prior Publication Data

US 2002/0068707 A1 Jun. 6, 2002

Related U.S. Application Data

(63) Continuation-in-part of application No. PCT/JP97/04468, filed on Dec. 5, 1997.

(30) Foreign Application Priority Data

Dec. 5, 1996 (JP) ............................................. 8-325763

(51) Int. Cl.$^7$ ........................ C07H 21/02; C07H 21/04
(52) U.S. Cl. ................................... 536/23.1; 536/24.31
(58) Field of Search ............................ 536/23.5, 24.31; 514/44

(56) References Cited

U.S. PATENT DOCUMENTS 5,378,464 A * 1/1995 McEver .................... 424/143.1

FOREIGN PATENT DOCUMENTS

| DK | 4238778 A | * | 11/1992 |
| EP | 269072 A | * | 6/1988 |
| EP | 915 156 |  | 5/1999 |
| WO | 99/26980 |  | 6/1999 |

OTHER PUBLICATIONS

Hillier et. al.; GenBank Acc: H71226; 1996, Genome Res. 6: 807–828.*
Duh; Accession No. U23946, 1996.*
Hettmann; Accession No. S71037, 1994.*
Kelly, et. al.; Accession No. X02228, 1993.*
Hillier et. al.; GenBank Acc: N89899, 1995.*
Hillier et. al.; GenBank Acc: H73595, 1996.*
TRick; Accession No. X52089, 1995.*
Hudson; Accession No. G24450, 1996.*
Hillier et. al.; GenBank Acc: T98890, 1995.*
Genbank Accesion No. SYNPBR328V, National Library of Medicine, accessed by PTO Nov. 30, 2000, Jul. 1993.*
Gerken, et al., May 23, 1995. Accession # L29874.*
Podgorski, et al, 1989. Mol Cell Biol ((9):3938–3950.*
Adams, etl. Aug. 1993. WO9316178–A.*
Gantt, Mar. 21, 1995. Accession # Z11508.*
Soares, et al., Apr. 13, 1994. Accession # T10350.*
Lindr, et al., Jan. 1995. Accession # M14618.*
Kraus, et al., Jun. 1991. WO9108214–A.*
Alberts, et al. Molecular Biologoy of the Cell, Third Edition. Garland Publishing, 1994.*
Ding, et al, 2000. J Exp Med, 191(2):213–223.*
N89899, EMBL (Aug. 15, 1996) XP002238226.
Database EMBL 'Online!, Accession No. AL023657, May 22, 1998, XP–00219247.
Sayos, et al., Nature, vol. 395, No. 6701 (1998), pp. 462–469.
Database EMBL Online, "Human Cosmid LUCA22", pp. 1–12, (Oct. 10, 1996).
Database SWISSPROT Online, "LUCA15", pp. 1–3, (Oct. 1, 1996).
Lai Kar Neng, et al., "Increased mRNA encoding for transforming factor–β in CD4+ cells from patients with IgA nephropathy", Kidney International, vol. 46, No. 4, pp. 862–868, (1994).
Database EMBL 'Online!, Accession Nr. AA772278, Jan. 31, 1998 (XP00217919).
Database EMBL 'Online!, Accession Nr. AA634469, Oct. 31, 1997 (XP002175920).
Database EMBL 'Online!, Accession Nr. AA381126, Apr. 18, 1997 (XP002175921).
Toyabe, et al., "IgA nephropathy–specific expression of the IgA Fc receptors . . . ", Clin. Exp. Immunol, vol. 110, No. 2 (1997), pp. 226–232.
Duque, et al., "Interaction of IgA with Fcα Receptors of Human . . . ", J. Immunol., vol. 159 (1997), pp. 3474–3482.
Ichinose, et al., "Detection of cytokine mRNA–expressing cells in peripheral blood . . . ", Clinical and Experimental Immunology, vol. 103, No. 1 (1996), pp. 125–132.
Plant Physiol, vol. 106 (1994), pp. 1241–1255.
Clin. Exp. Immunol. vol. 103 (1996), pp. 125–132.
Kidny International, vol. 2 (1996), pp. 571–577.
FEBS Letters, vol. 351 (1994), pp. 231–236.

* cited by examiner

*Primary Examiner*—Joe Woitach
(74) *Attorney, Agent, or Firm*—Fitzpatrick, Cella, Harper & Scinto

(57) ABSTRACT

The present invention relates to a novel DNA related to IgA nephropathy obtained by a differential display method [*FEBS Letters*, 351, 231 (1994)] taking note of an mRNA whose expression level fluctuates in leukocytes of IgA nephropathy patients in comparison with leukocytes of healthy persons, a process for isolating the DNA, a method for detecting the DNA, a novel protein encoded by the DNA, an antibody recognizing the protein, a method for detecting the protein, and diagnosis and treatment of IgA nephropathy.

5 Claims, No Drawings

SEQUENCE LISTING (1) GENERAL INFORMATION:

(iii) NUMBER OF SEQUENCES: 111

(2) INFORMATION FOR SEQ ID NO:1:

(i) SEQUENCE CHARACTERISTICS:
      (A) LENGTH: 4276 base pairs
      (B) TYPE: nucleic acid
      (C) STRANDEDNESS: double
      (D) TOPOLOGY: linear (ii) MOLECULE TYPE: cDNA (vi) ORIGINAL SOURCE:
      (A) ORGANISM: human
      (G) CELL TYPE: leukocyte (xi) SEQUENCE DESCRIPTION: SEQ ID NO:1:

```
TTCTACCGTT TTTTCCCTGC TTTCTATTCC AGGTCAGTCT TCACTGTTTC CG ATG GAA      58
                                                         Met Glu
                                                           1

GAT GGA TTC TTG GAT GAT GGC CGT GGG GAT CAG CCT CTT CAT AGT GGC      106
Asp Gly Phe Leu Asp Asp Gly Arg Gly Asp Gln Pro Leu His Ser Gly
        5                  10                 15
```

-continued

| | | |
|---|---|---|
| CTG GGT TCA CCT CAC TGC TTC AGT CAC CAG AAT GGG GAG AGA GTG GAA<br>Leu Gly Ser Pro His Cys Phe Ser His Gln Asn Gly Glu Arg Val Glu<br>   20                            25                            30 | | 154 |
| CGA TAT TCT CGA AAG GTG TTT GTA GGC GGA TTG CCT CCA GAC ATT GAT<br>Arg Tyr Ser Arg Lys Val Phe Val Gly Gly Leu Pro Pro Asp Ile Asp<br>35                         40                          45                        50 | | 202 |
| GAA GAT GAG ATC ACA GCT AGT TTT CGT CGC TTT GGC CCT CTG ATT GTG<br>Glu Asp Glu Ile Thr Ala Ser Phe Arg Arg Phe Gly Pro Leu Ile Val<br>                55                            60                          65 | | 250 |
| GAT TGG CCT CAT AAA GCT GAG AGC AAA TCC TAT TTT CCT CCT AAA GGC<br>Asp Trp Pro His Lys Ala Glu Ser Lys Ser Tyr Phe Pro Pro Lys Gly<br>                70                            75                          80 | | 298 |
| TAT GCA TTC CTG CTG TTT CAA GAT GAA AGC TCT GTG CAG GCT CTC ATT<br>Tyr Ala Phe Leu Leu Phe Gln Asp Glu Ser Ser Val Gln Ala Leu Ile<br>                85                            90                          95 | | 346 |
| GAT GCA TGC ATT GAA GAA GAT GGA AAA CTC TAC CTT TGT GTA TCA AGT<br>Asp Ala Cys Ile Glu Glu Asp Gly Lys Leu Tyr Leu Cys Val Ser Ser<br>100                       105                        110 | | 394 |
| CCC ACT ATC AAG GAT AAG CCA GTC CAG ATT CGG CCT TGG AAT CTC AGT<br>Pro Thr Ile Lys Asp Lys Pro Val Gln Ile Arg Pro Trp Asn Leu Ser<br>115                       120                        125                    130 | | 442 |
| GAC AGT GAC TTT GTG ATG GAT GGT TCA CAG CCA CTT GAC CCA CGA AAA<br>Asp Ser Asp Phe Val Met Asp Gly Ser Gln Pro Leu Asp Pro Arg Lys<br>               135                       140                        145 | | 490 |
| ACT ATA TTT GTT GGT GGT GTT CCT CGA CCA TTA CGA GCT GTG GAG CTT<br>Thr Ile Phe Val Gly Gly Val Pro Arg Pro Leu Arg Ala Val Glu Leu<br>                   150                       155                        160 | | 538 |
| GCG ATG GTA ATG GAT CGG CTA TAC GGA GGT GTG TGC TAC GCT GGG ATT<br>Ala Met Val Met Asp Arg Leu Tyr Gly Gly Val Cys Tyr Ala Gly Ile<br>               165                       170                        175 | | 586 |
| GAT ACC GAC CCT GAG CTA AAA TAC CCA AAA GGA GCT GGG AGA GTT GCG<br>Asp Thr Asp Pro Glu Leu Lys Tyr Pro Lys Gly Ala Gly Arg Val Ala<br>180                       185                        190 | | 634 |
| TTC TCT AAT CAA CAG AGT TAC ATA GCT GCT ATC AGT GCC CGC TTT GTT<br>Phe Ser Asn Gln Gln Ser Tyr Ile Ala Ala Ile Ser Ala Arg Phe Val<br>195                       200                        205                    210 | | 682 |
| CAG CTG CAG CAT GGA GAG ATA GAT AAA CGG GTA AGC CTT ATA CTA CAT<br>Gln Leu Gln His Gly Glu Ile Asp Lys Arg Val Ser Leu Ile Leu His<br>               215                       220                        225 | | 730 |
| TTT GGA AAA TTC TAGAAATGGT CCTCTAAATG TGTGATTACC AATATTAGAA<br>Phe Gly Lys Phe<br>               230 | | 782 |
| CGGGAGCATT TTATGACAAT AAAGTGACAG CTGACAATTT TGCCTATAGA GTTAATTATG | | 842 |
| GTCTATAATA CATGAAATAA TGTCCTATGA ATTTCTTTTA TCTTTCAGTT TTTTGAGTAG | | 902 |
| CCTAATCAGA ACACTACAAT TTACTTGAGT TAATTTAATC TTCTCTAACT TCCATTCAAT | | 962 |
| CTCAATCCAT CCGTCCATTC ATTCACTTAG TTTGTAAGTC ATTCAATAAA TATTTACTGA | | 1022 |
| ATCCTTTGTT CTGTGTTATA TCAAGTATAC AAACAGGAAT GCCCTTGAGG TTTCCTGCCC | | 1082 |
| TTTTTTTTGT TTGTTTTTTA ATCCTGGGAC ATAGGGAAGA CCTCAGCAAG CCCTATTTCT | | 1142 |
| CAATGAATTG TACTCACAGA TTTCTTTTTT TTTTTTTTT TCTTTTTCCA CAGCCGCCAC | | 1202 |
| CTCTCACCGA TTTATTCCTT AGCTTGGTGT TCATGTATT CAACAAACGT TTAGTGCTT | | 1262 |
| AGGGCAAGAA GTTCCTGTCC TCATGAGTTT ATTTCCTAGC AGATAGAACT GTATCACTTG | | 1322 |
| CCAGTACTAC TCAGAGTGTG GCCTGTGGAC TGACCTCCAG TCTGTAAACT TAGTTTGTAG | | 1382 |
| TGAGATAGGA ATTTAGACCA GAATGTGTAA TCAACCACAT TACTGGGCAC AATGTTTGGT | | 1442 |
| CCAGCTGGCG ATTTTTTTTT CATAGAAAGC CTTTATTGAT GAGGGAAGCA ATATATTGAT | | 1502 |

```
TTATATTTTG GGGTCACCTT TTTATTTCAT GGCACACTGG CACTTTCATG CATGCTGACT      1562

TTGATATCCA TCACTCTGAG GCATTGTGCT AAAATAGATT GATTTTATCG TGTTGTTCTC      1622

AATTCAAGAT GTAAAAATCA TCAAGTCAGT AGCAGTTTTT GCTTTTTATG TTTCATGTCA      1682

TGTACAGTCT ACTTCACTGG CAGTAAAAAA ATTTAAGATA GTGGTGGTCA TCCTACAAAC      1742

TGTGAATCTA TTAAAGAGAA AAGTATCTGT TCTATTCTAA GCATGGGGGA GGGACAAGAT      1802

TAGTATGTTA ACATGCCTAC TTTGTTTGTT TGAGATGGAG TCTCTCTCCG TCACCCAGGC      1862

TGGAGTGCAG TGGTACAGTC TCAGCTCACT CCAACCTCTG CCTCCCGGGT TCAAGTGATT      1922

CTCCTGCCTT AGCCTCCCGA GTAGGTGGAA TTACAGGCAT ATACCACCAT GCCCAACAAA      1982

TGTTTGTATT TTTAGTGGAG ACAGGGTTTC ACCGTGTTGG TCAGGCCAGT TTCAAACTCC      2042

TGACCTCAAG GGATCCACCT GCCTCACCCC CTCAAAGTGC TGGGATTACA GGCATGAGCC      2102

ACCCACCATG CCTGGCCTAC TTGGTTTTTT ATGCACACTA AAAATACCT ACATCTCACT       2162

GCCTTATTCC AACATAAGTT TCAGAGCTGT GGGATTGGTC ATTAGAAATT CAGACTGAAT      2222

TTGTGTTCCT CTGCAATGAA ATCCTTTGCC CAGTGTTCAT GTCACTCTGT AGACATTATG      2282

GAGCAGCCTA GAGGCCAGAA GCCCAGTGCT CTCCTTATGC CTGCTCTTCC TGGGCTTCGT      2342

GACACTCTTC TTCTCCTTTT GTACTTTTAT TTTTTTAGTT AAAAAATTTT TTTTAGAGGG      2402

AGGGTCTCAC TCTGTCACCC AGGCTGGAGC ACAGAATCAC AATCATGACT CACTGCATGT      2462

TCTTCTCCTT TTGTTCATGG CTAATCTTGG TCAGGATTCC TTGTCAGAGC TGGGTGGCAC      2522

CAGTGCTGGT GACAGCCTGC TGTAAGGGAG TTTCAGCCAT GAATCTCTCC AGACTAAAAA      2582

TAACCAGCTC TTTTCTAGCT GATGAATTAA TAACCAGGTG ACTGTTAATG CTTGAAAGGT      2642

TCACATGACA GGTTGGCCGA TAGAACGCTG GAACAGGCCC AGTTTTAGAA ATTCACCTCT      2702

GACTTTTAGA CTCAGGTGAA CCATTCTTAC TGAGAAAGAA CAAAGCAGGG TTTTAGACTG      2762

TGAATCCTAT GGCTGCATCT TTTTTTTTTT TTTAACAGAG TTCCAGGTTT GTGATTATAA      2822

CCCAACATGT GTACACTATA AATAGAAACC ACGAGCCAGG CTTTTTACGA CAGCTCAGAA      2882

TCTTGTGACG CAGTAGTCAG GCATCTTCAC ACCGACTTGA ATATTGAAGT GCAGTTGTGT      2942

GGAACTTGGA TCATCTTAGT TGATTTTGTT TAAATTATGA TTCCACATAT GACAAAAATC      3002

CAGATCCACT AATTAAAATG AGGGTTTATG TCTATGAATA ATCTCCTGTG GGTTAATCT       3062

CATAACATTC TAGTCTAAAC AGTTGGCTTC ACTTCATGAT GTCTGCTCAA ATCCTTTTTC      3122

CTTTAAAGGA TGTTTATTTA ATAAGAAAAA AAATGTAAAA TGATAGATAA TAAAAGCCTT      3182

ACTAGGTTCT TAAAAGATGA ACTATCCATA TTTCAGTAAA TGAATAATTA GTCCTTCCTC      3242

TTTGGGCACC TTGGAACAGA TTCATTCAGA TAGTGGGTGG AAATGTACAT GTATGGTAAG      3302

CATTGCTGGC CTAGTCACTG AAAAATGTAA ACTCTTATTT TTGATTGCAG GTGGAAGTTA      3362

AGCCATATGT CTTGGATGAT CAGCTGTGTG ATGAATGTCA GGGGCCCGT TGTGGGGGA       3422

AATTTGCTCC ATTTTTCTGT GCTAATGTTA CCTGTCTGCA GTATTACTGT GAATATTGCT      3482

GGGCTGCTAT CCATTCTCGT GCTGGCAGGG AATTCCACAA GCCCCTGGTG AAGGAAGGCG      3542

GTGACCGCCC TCGGCATATT TCATTCCGCT GGAACTAAAG GATAACTGCA GTGCTCATTT      3602

TCAGGCCTCA GAATAAGTGC ACTCTTCTGT TCATTCTGAC CCCTTCCTCA ACCTCTTCAC      3662

GCTGGCATGT CCTTTTGTAG CAGTCTGTAA CTTAACTATA GTATAATGAA AAGAATGACC      3722

TATAATATAG GTGTTTTGTA GATTCTTGTG TCACTGCAAA CAATATGAAC TCCTTTTTCG      3782

TATTGCCATC GGGTTGCATG GAAGTTTTAT TCTCTTGTTT TGCTGGAAAC CAAGAGGATC      3842
```

-continued

```
CAAACTTCCT GCAACATTTT CTTAGAGGAG AGAGAGAAAT ATTAAAAGAG AAATGAAACA    3902

ATAGAGTATT TTGGGTTTTT AATTAAATTA TTGTTAATAA TATAACATAT AAGAATACTT    3962

TTATTAAAAT AACCATGCAA CAATAACACT ATCGGTCTAT CTGACAGTTT TTCCCCCAGG    4022

GAAGTGCTTT TGCCTTTTCC TTTCTTTTTT TTTTTTTTTC ATCTTTTTTG TTCTCTCTCT    4082

TTTTTCCATC CCTTTTTAAT TTTTTTAACA GCAATGGAGG AAGTTAACAA TTTTTAATGG    4142

AAAGAGCATG TTAGAGCAAA CAAATGCATA AGCAAGACTG AGCAGCATTA TAATTAATTT    4202

TCAGGGTTTT GAGGCTGAAC ATAATTTCAT TATCCCTCAA AAAGTTACCA CCACATCAGA    4262

AAAAAAAAAA AAAA                                                      4276
```

(2) INFORMATION FOR SEQ ID NO:2:

(i) SEQUENCE CHARACTERISTICS:
        (A) LENGTH: 2689 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:2:

```
GTTGGAGGTT CTGGGGCGCA GAACCGCTAC TGCTGCTTCG GTCTCTCCTT GGGAAAAAAT     60

AAAATTTGAA CCTTTTGGAG CTGTGTGCTA AATCTTCAGT GGGACA ATG GGT TCA       115
                                                 Met Gly Ser
                                                   1

GAC AAA AGA GTG AGT AGA ACA GAG CGT AGT GGA AGA TAC GGT TCC ATC      163
Asp Lys Arg Val Ser Arg Thr Glu Arg Ser Gly Arg Tyr Gly Ser Ile
      5                  10                  15

ATA GAC AGG GAT GAC CGT GAT GAG CGT GAA TCC CGA AGC AGG CGG AGG      211
Ile Asp Arg Asp Asp Arg Asp Glu Arg Glu Ser Arg Ser Arg Arg Arg
 20                  25                  30                  35

GAC TCA GAT TAC AAA AGA TCT AGT GAT GAT CGG AGG GGT GAT AGA TAT      259
Asp Ser Asp Tyr Lys Arg Ser Ser Asp Asp Arg Arg Gly Asp Arg Tyr
                 40                  45                  50

GAT GAC TAC CGA GAC TAT GAC AGT CCA GAG AGA GAG CGT GAA AGA AGG      307
Asp Asp Tyr Arg Asp Tyr Asp Ser Pro Glu Arg Glu Arg Glu Arg Arg
             55                  60                  65

AAC AGT GAC CGA TCC GAA GAT GGC TAC CAT TCA GAT GGT GAC TAT GGT      355
Asn Ser Asp Arg Ser Glu Asp Gly Tyr His Ser Asp Gly Asp Tyr Gly
         70                  75                  80

GAG CAC GAC TAT AGG CAT GAC ATC AGT GAC GAG AGG GAG AGC AAG ACC      403
Glu His Asp Tyr Arg His Asp Ile Ser Asp Glu Arg Glu Ser Lys Thr
     85                  90                  95

ATC ATG CTG CGC GGC CTT CCC ATC ACC ATC ACA GAG AGC GAT ATT CGA      451
Ile Met Leu Arg Gly Leu Pro Ile Thr Ile Thr Glu Ser Asp Ile Arg
100                 105                 110                 115

GAA ATG ATG GAG TCC TTC GAA GGC CCT CAG CCT GCG GAT GTG AGG CTG      499
Glu Met Met Glu Ser Phe Glu Gly Pro Gln Pro Ala Asp Val Arg Leu
                120                 125                 130

ATG AAG AGG AAA ACA GGT GAG AGC TTG CTT AGT TCC TGATATTATT          545
Met Lys Arg Lys Thr Gly Glu Ser Leu Leu Ser Ser
                135                 140

GTTCTCTTCC CCATTCCCAC CTCAGTCCCT AAAGAACATC CTGATTCCCC CAGTCTTCAA    605

GCACATGAAT TCAGAATGAA AGGTTTGCCA TGGCTAAGGA ATGTGACTCT TTGAAAACCA    665
```

-continued

```
TGTTAGCATC TGAGGAACTT TTTTAAACTT TGTTTTAGGG ACTTTTTTTT CCTTAGGTAA      725

GTAATGATTT ATAAACTCCT TTTTTTTTTT TTGACTATAG TCGGTTGCAT GGTTACTTTA      785

AGCGTGGAAT CAAATGGAGT GGCATTTAGT TCAGGCGGCT TGTTCCTTGC CATGGCAAAG      845

TATCAAGAAG ATCCCCAAGT CAAGTCACAT TTGTAAAGCT GCTTCCCAAT TGGCTTTGTC      905

ACGCAGTGTT GAAGCAGTGG GAGAGAGATT CACCTGTTAT AAAGGAACTG ACTAACACAA      965

GTATCCCGTC TATATCTGAA TGCTGTCTCT AGGTGTAAGC CGTGGTTTCG CCTTCGTGGA     1025

GTTTTATCAC TTGCAAGATG CTACCAGCTG GATGGAAGCC AATCAGGTTG CTTCACTCAC     1085

CAAGTCTAGA TATTCATGAA AATGGAACAA GTCTGTACAA TTTTAAAAAA AGGTTGAAGG     1145

AGTGGTTTGT TCCAAAGGAG TGACTTTTTT TTAAAAAAAA AAGCTTTGTA TATATTAAAA     1205

TTGATGTTAC TAGAATAAGT ACAGTACCAA GGACTTCATT ATAGAATTTG TTCTGCCTTT     1265

AAACATGGCT ACCTACCTGG CAGGGCTTTG TTAACTACTG AATACCTGTC TGGTAATCAC     1325

TAAAACATCT TAATGTTTCC CTTTTTTCTA GTTTGTTATA TTCCTATTAT GTCCATTGAG     1385

AGTAAGCTTA GTATATCAAA CTCTCCATTT GACAGTGAAG AGAACATAGT GAAAGTCTGT     1445

GGCGGCATTT TTATAAGTAA TTCCTTATTT CTGCCTGAAG ACCACAAAGC CTCCTGGAGG     1505

CGTAACTGCT CAGACCGGTC TTCAGGGAAT ATTTAAGGAC TTAGTGGAAT TTATGAACAA     1565

TAAGTCTGAT GAGATTAGCC TGGGAGTGGT GTCCTGCAGC TGTCTAATCT AGTTAGAGTG     1625

GCATTAACAT TCTAATCTCC TTGAGAATGC CTTTTATAGT CTGTTCAAAG CAAGTCATTG     1685

ATGGTTCTTC GAGGTAGTGT TAACTGAAGT GTTCTTCAGT TTGTCAAGAT AATGTTCAGT     1745

GCTTGGCACT TAAATAACAT TTTTTGCAAG AACTCCAAGG CACATTATTG AATGCCTTTA     1805

ACCAAGTGCA TTCTGGGAAG TTTGCTTGAC TCATTATCTT GCTTTTCTGC AGCATTCTGT     1865

GATTTGAGTC ATCCATGAAT CCATGAATAA AAGTTACATT CTTTGATTGG TAATATTGCC     1925

ATTTATAACA AGACTCACTA ATGAGGGTAT CACTTTGACT GACTGATTTG TTAAAGTTTT     1985

TAAGCCTCTC ATTTTCCTAA CCCAGAAATC ACAGCCTGAT TTTATTAAAA GTAGAGCTTC     2045

ATTCATTTCA TACCATAGAT ACCATCCTAG TAAATCCAGA ACATATACAA GGTTCATGTG     2105

AGTCTGCTTT CTTGACATGA TAGCATTGTT TGATGCAGTG GATATGTCAG AATGACTAAC     2165

CTAGGAGTTT AAAACTCCTA AGAAACTAAA ACCTGTAAGA CATTTAAAAG TCTCCACAAT     2225

TTTAATGTAT ACAAAGCTAT GTTACTGTGT AACACATTAC AGTTCAAATT CACTCCAGAA     2285

ATAAAAGGCC AGTAGGATTA GGGACTCACT GGTAGTTTGG AGTCTCCCAG CACACATCCC     2345

TCCTAGTGGG ATGATCTATT CACATATCTC CCAGCTTTTT TATTTTGCT TCTGTATATC      2405

ACAGTGAGTG GATGGCCCTT CAGCTTTTTC TCTCCTGGCC AGACATGCAG TCTTGCCTTT     2465

AGATATCGCA GAGACAAAAT TCACAGCATG TCTTAAATCT TCCAGGATTT GCAAGAACCA     2525

AATTGCTCAA CAGTATGTAT GTTTAGAGGG GTTAGACTCC TTTTTAAAAT CTGGATATCT     2585

AACCACCTAC TTAAATCTGT TTGATAGTGT CAAACCACCC CCACCCTTGA TCCTCCCACC     2645

CCCAAAAAAA AAAAAAAAA AAAAAAAAA AAAAAAAAA AAAA                        2689
```

(2) INFORMATION FOR SEQ ID NO:3:

(i) SEQUENCE CHARACTERISTICS:
        (A) LENGTH: 2981 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
    (A) ORGANISM: human
    (G) CELL TYPE: leukocyte (xi) SEQUENCE DESCRIPTION: SEQ ID NO:3:

```
CCTCTCTCTC TCTTTCACAG AGTCTTGCTC TGTCGCCCAG GCTGGAGTGC AGTGGCACAA      60

TCTCACTGCA AGCTCCGCCT CCTGGGTTCA CGCCATTCTC CTGCCTCAGC CTCCCAAATA     120

GCTGGGACAA CAGGCACCTG CCACCACGCC CGGCTAATTT TTTGTATTTT TAGTAGAGAC     180

AGGGTTTCAC CATGTTAGCC AGGATGGTCT CAATCTCCTG ACCTCGTGAT CCACCCGCCT     240

CAGCCTCCCA AAGTGCTGAG ATTACAGGTG TGAGCCACCA CGCCCAGCCA CATCTTTCTT     300

TCTTTCTTTT TGGTTTTTGT TTGTTGTTTG AGACAGGGTC TTGCTCTGTC GCCCTGGCTC     360

ACGTGAACCT CCCACCTCAG CCTCCCAAGT AGCTGAGACC ACAGGTGTGA GCCACCACTC     420

CTGGGTAATG TTTGTATTTT TTGTAGAGA  TGGGGTTTCA CCGTGCTGCC CAGACTGCTC     480

TCAAACTCCT GGGCTCAAGT GATCCACCTG CCTTGACCTC CTAAAGTGCT GGAATTACAG     540

GTGTGAGCCA CCGTGCTCAG CCGAGTGTCT TTCGTATGTT TTCTGAGCAC GTGGATTTCC     600

ATCTCTCTGC ATTCTCTGTT CATCTCAGCC TGTTTGTTCC ATTGAGATAA ATGACTTTTT     660

CTTGGTAACT TAGAGTACTT TGTGTATTTA CAGGTTAATC CCTTATCAAT TTATATCAGT     720

TGCTGCTATC TTTTCTTAGA TTTTTCTTTT CATTTTAAAA ATTACATTGT TTCAATGAAC     780

AGAATTTTTA AGTTTAACG  TAGTCCACTT TGTCCATTTT CTTTATGACC GGTGCATTTT     840

AGGGTCTTGT TTAAGAAATC GTTCTTTATC CTGAGGTCAT AAAGATAGTC TACTGTATTT     900

TCTTTTAAGA GCTGAAAAGG TGTTTTATAT TTAATTTATT TGGGATTGGC TTTTGTGTGG     960

TGGGATAAG  GATCACAATT TTATTTCATT TTTTTTCCAC TTGGTTATGC CAGTGGCCCC    1020

ATTTCCATTT TTTGAATAGT CTTTCTGTGC AGAAAAGACT TCACTAGCAG AGAAGTCCTG    1080

AGACTTACCC TTCAAAAGGC CCCATTCACA AGGCTAGCAC TTGGCGTGCA TCTGAGAACC    1140

TGGATTTTGG GGTGGTTCCT ATAATGTGGT GTATGCTGAA CACCCACCTT TCCTTCTGGG    1200

AGTCTGGAAT TTGGGTATAT GTTGGACAGA GGCTGCCTAA GTGACCAGCT TCAACAACAG    1260

CCCTGGGTGC TGGGTCACTC ATGACCCATA GACAAA ATG CCA CAC ATG TTG TCA      1314
                                      Met Pro His Met Leu Ser
                                       1               5

CAG CTT ATT GCT GGA GGA GTT AGC ACA TCC TGT GTG ACT GCA CTG GGA      1362
Gln Leu Ile Ala Gly Gly Val Ser Thr Ser Cys Val Thr Ala Leu Gly
           10                  15                  20

GAG GAA ACT GGT GCC TGG TTC CCT GTG TAT TTG TCC CAC GCC TCC AGT      1410
Glu Glu Thr Gly Ala Trp Phe Pro Val Tyr Leu Ser His Ala Ser Ser
       25                  30                  35

CCC TTT GCT GAT CTC GTT TTT TGT CCT TTT GCT GAG ATA AAT CAC AGC      1458
Pro Phe Ala Asp Leu Val Phe Cys Pro Phe Ala Glu Ile Asn His Ser
   40                  45                  50

CAG GAG TAT GAC AAT ATG CGG GGT CCT GTG AGT CCT CCT AAC AAA CAG      1506
Gln Glu Tyr Asp Asn Met Arg Gly Pro Val Ser Pro Pro Asn Lys Gln
55                  60                  65                      70

TTC AAT CTG GGG GTG ATC TTT GGG ATC CCC AAC AAC TGT CGT TTC CCC      1554
Phe Asn Leu Gly Val Ile Phe Gly Ile Pro Asn Asn Cys Arg Phe Pro
               75                  80                  85

ACT GAT AAT AAA ATA ACT GAG AAG CAG CTA TTG GGC AAT GTT CTG AAC      1602
Thr Asp Asn Lys Ile Thr Glu Lys Gln Leu Leu Gly Asn Val Leu Asn
               90                  95                 100

TAC CCT TGAACATTCA TGTCTTCATC TGAACATCCA TCTACTACCC CTGATTTTTT       1658
Tyr Pro
   104
```

```
CAGTGCAGGG TGCATATCCT GTATCACCCA ATAAATGGTC ATTGATCACC ATAGGAAAGG    1718

AACAGTGAAA GCTCCACGGT GGTTTGGAGG AAGGTGGCAG GCATTCAGCG GTAACTTTTT    1778

TGAGCAGATA GATTTTATGT TTTTGCAATG AGTGAAATAA ATTTTCCCAT ATCTATTTAA    1838

GGTTGGCAAT CATTATCTTT TTATCATCTT GGAACATTTG GAATTCCTTT AATATGTTTA    1898

GTTAGGAATT TTCTACCTTC CTCATCTTGT CCGATAGTTT AAAATCCCAC AGTTATTTCA    1958

CGGGCTCCTC ATACCTGCCT GTGTGATTTC TAACATGTCA CGCTATGCAA CCAGTTGCTT    2018

TTACTTGTAG AGTGTTTCTT TAGGTAATAG CTTATTATTG GTTATGTGAT TACAGTGTGT    2078

TAAAGACAGG TCTGTAGTTA TGTAAAATGC CGTTTCTCTG AGTATCATGG TCATTTCCAC    2138

ATATTTCTCT ATTCATGTAT TTGTAAGAAT ATATCTATTT TTGCAGTATT TTATTTATTT    2198

ATTTTATTTT ATTTTCTGAA ACGGAGCCTT GTTCTGTCAC CTAGGCTGGA GTGCAGTGGT    2258

GTGATCTCGA CTCACTGTGA CCTCCCCCTC CCAGGTTCAA GCGATTCTCC CGCCTCATCC    2318

TCCCAAGTCA TTGGGATTAC AGTCACGTGC CATGAAGCCC TGCTAATTTT TTGTATTTTT    2378

AGTAGAGACA GGATTTCACC ATGTTGGCGA TGCTGGTTTC GAACTCCTGG TTTCGAACTC    2438

CTGACCTCAA GTGATCCACC TGCCTCGGCC TCCCAAAGAA CTGGGATTAT GGGCGTGAAC    2498

CACCACGCCA GGTCAGTTTT GCAGTGTTTT AAATACTGTT GTCTTTGAGA GGAGAGAGGC    2558

ACGCACATAG ACTATGGTGA TTACCATCAT ATACTGGAAA GTGCAAAGTG TAGCGCAGTT    2618

AACTGTGAGC CATCTCATCA AACCCTAACA GATGTCTCAT TTGTCCATAA AGGGGCTTCT    2678

GTCCCATAGA AATTCATGTA CCCAACCTAC TCTTCAACCA TGATTTTTCT CTGATGGCCT    2738

GTGTGAACAG ATTAATGGTG TCCATCTAAT TCCTTCCCCA CTGGGGGAAA GCAAATCATC    2798

AGGCCCATTG CAAAAACTGC TCTTGGTTGA GCTTCCTGCC TTAAATCATA CCCACAGTGA    2858

ATGGCGTCCC TTTATCACCG CTAATGACTC TGACATCTCT CTCCACTCAC ATGTGAGCCT    2918

CCTCAGCTCT CGATAAACAA GTCTGTCTCG GTTCATTTAT TCTACAAAAA AAAAAAAAAA    2978

AAA                                                                  2981

(2) INFORMATION FOR SEQ ID NO:4:

(i) SEQUENCE CHARACTERISTICS:
        (A) LENGTH: 1461 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:4:

AATTCGGCAC GAGCAGCTTT CTAGTTGGAT TAGGCAACAG AATCCTTTGA AAATGTGTGT     60

GCACAGACCA GGTGGCTCTC TGGGCCAGTG TACTCTGAAA GATGTGTGTC CTGGCCTAGC    120

TGGTTGAGGA AAAGCAGGGC AAGCCTAGCC AAATCACACA TCTTGAACAG CCCTCATTCG    180

TTATACTAAC TTTCCCACCT TCTGGTGTGT ATAGGAGATA AAGATGGCAG ACGTGCTATT    240

AGGCTGCCAA TGGAGTGGG CTCTGATATG GTCTTTCAAA T ATG AAT CAC CCC TGG    296
                                             Met Asn His Pro Trp
                                              1               5

CAT GTG TGT TTC CTG TTT AAG GTT CTC AGG TAT TAC CCA ACT GCA CCA    344
His Val Cys Phe Leu Phe Lys Val Leu Arg Tyr Tyr Pro Thr Ala Pro
        10                  15                  20
```

| | | |
|---|---|---|
| ATA TTA AAA TGG ACA CAT ACC GTG TCA TGC AGT TGG TGC CGA AGT GTT<br>Ile Leu Lys Trp Thr His Thr Val Ser Cys Ser Trp Cys Arg Ser Val<br>25                             30                            35 | 392 |
| TTA AGG GAA GTT GTA GGC AAT GTG AGT TTA TCA GAA AAC TTC ACC ATA<br>Leu Arg Glu Val Val Gly Asn Val Ser Leu Ser Glu Asn Phe Thr Ile<br>40                             45                           50 | 440 |
| TCA GCA TTT TGC CCT GAG CTT ACA CCA TTC CCA GAT CAA GGT ACA AGC<br>Ser Ala Phe Cys Pro Glu Leu Thr Pro Phe Pro Asp Gln Gly Thr Ser<br>55                             60                           65 | 488 |
| ACA ATG ATT TCC TTT CTT GAA AAG TTC AAC AAA AGC AAG AGA GAG AGA<br>Thr Met Ile Ser Phe Leu Glu Lys Phe Asn Lys Ser Lys Arg Glu Arg<br>70                           75                          80                         85 | 536 |
| TTG GAG TTG ATG CTG CAT TTT TAT TCT GTG TTA AGT CTT GAA CCT GCT<br>Leu Glu Leu Met Leu His Phe Tyr Ser Val Leu Ser Leu Glu Pro Ala<br>90                           95                           100 | 584 |
| GCT GCT GAA CAT TGG TCA GGG GAA TTT GAG AAG TGG AAA GTG GGC TTT<br>Val Ala Glu His Trp Ser Gly Glu Phe Glu Lys Trp Lys Val Gly Phe<br>105                         110                         115 | 632 |
| TTT CAC CCT TTG AAA AGA GAG GAT GGA TTC TTC ACC AGA ACT GAC ATT<br>Phe His Pro Leu Lys Arg Glu Asp Gly Phe Phe Thr Arg Thr Asp Ile<br>120                       125                         130 | 680 |
| TAAAAAAGT CAGCGTGGCA CGTTTTAGTA TGTGTGGCAG ATCTAAASAG ACAATATTTT | 740 |
| GATCTCAGGA GTGTTTATTC TTGAACCATT TTCAGAACTC TAAGATTTGA GAAATAATAA | 800 |
| AATATTGACC ATCCTTCAAA GAGAAAAACA CAGGGCGATC TTTGGCATAG CCTGTCATTT | 860 |
| TGCTCACATT TCACTTCTCT CTCTCCAACT TCAGAGCCCC TGCTGTGGAA CAGGTGCTGT | 920 |
| GCTGGGTGGC AGGGGAGGTC TCTGGCTTTT TTTTTTTTG ATCTCCGTCT TAACATCTAG | 980 |
| CCTACTGGAG GAAGTGTATT TAATCATCCA CTTATCTGTT AACAATTATC TCTGAGGGCC | 1040 |
| CGTCACATTC AGAGAAGATT CTAGGTTCTC TACAAGTATC CTCTCACTGT GTACATACTA | 1100 |
| AATCAACATC CTGCTGGATT TCCCCCAGAC ATCTCCCTTC ATCACCATTG AGAGTATCC | 1160 |
| TCTAATTGCC AGCCCTATTC ACCATACTCA TCTCATTTGA TCTGGAGTTT TCTGAGAGTG | 1220 |
| ACCGGGGGTG GGATGGACAG GATAATTTAG CAAGAGTGTA TAAGTAAAAT CTATATAATA | 1280 |
| AAAGTTATCT CCCTGTGCCC CCCATGATCT ATTCTTTATG TAGCAGTCTG AATGAGATTT | 1340 |
| TCAGAAACAA GAACCACTTT ACCTTAGTCT CTTCTTCTTC TTCTTCTTCT TTTCTTTTCT | 1400 |
| TTTTTTTTAG TATTATGGGC AACAGAGCAA GACCCAGTCT CAGGAAAAAA AAAAAAAAA | 1460 |
| A | 1461 |

(2) INFORMATION FOR SEQ ID NO:5:

(i) SEQUENCE CHARACTERISTICS:
        (A) LENGTH: 3329 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:5:

| | |
|---|---|
| CCAAAGTGCT GGGATTATAG GCATGAGCCA CTGCGCCCGG CCAGAATACC CTATCCTTAA | 60 |
| ACATGAATTT AGGGGAGGGG AGGACACAAT TCAATCTATA ACAACTATCA CTGGCTGATT | 120 |
| TTGGCAGAGG CCTGTGGCCT CCAGTATTTT GAGGGAGCTG AGGGCCACTG ATCTCTCCAT | 180 |

```
ATGCTCTCAA CATCATGGGA CTAGTAGGAT GAAAGCAAGC CTCAGACCAG ATTCTACCTC      240

AAGCAGGCAC ACAAACATTC ATGCAGCTTC TACTTGGAGC CTGATGAAGT TCAAATTGTT      300

TGTCCTCTGA GGCTCTCTTT GCATGGAAAT TTCTCCCATG ACAGATGAGA AAGTTCTGGG      360

GCAGCATTCA GCTTTCTAGT TGGATTAGGC AACAGAATCC TTTGAAAATG TCTGTGCACA      420

GACCAGGTGG CTCTCTGGGC CAGTGTACTC TGAAAGATGT GTGTCCTGGC CTAGCTGGTT      480

GAGGAAAAGC AGGGCAAGCC TAGCCAAATC ACACATCTTG AACAGCCCTC ATTCGTTATA      540

CTAACTTTCC CACCCTCTGG TGTGTATAGG AGATAAAGAT GGCAGACGTG CTATTAGGCT      600

GCCAATGGGA GTGGGCTCTG ATATGGTCTT TCAAAT ATG AAT CAC CCC TGG CAT        654
                                          Met Asn His Pro Trp His
                                           1               5

GTG TGT TTC CTG TTT AAG GTT CTC AGG TAT TAC CCA ACT GCA CCA ATA        702
Val Cys Phe Leu Phe Lys Val Leu Arg Tyr Tyr Pro Thr Ala Pro Ile
            10              15              20

TTA AAA TGG ACA CAT ACC GTG TCA TGC AGT TGG TGC CGA AGT GTT TTA        750
Leu Lys Trp Thr His Thr Val Ser Cys Ser Trp Cys Arg Ser Val Leu
        25              30              35

AGG GAA GTT GTA GGC AAT GTG AGT TTA TCA GAA AAC TTC ACC ATA TCA        798
Arg Glu Val Val Gly Asn Val Ser Leu Ser Glu Asn Phe Thr Ile Ser
    40              45              50

GCA TTT TGC CCT GAG CTT ACA CCA TTC CCA GAT CAA GGT ACA AGC ACA        846
Ala Phe Cys Pro Glu Leu Thr Pro Phe Pro Asp Gln Gly Thr Ser Thr
55              60              65              70

ATG ATT TCC TTT CTT GAA AAG TTC AAC AAA AGC AAG AGA GAG AGA TTG        894
Met Ile Ser Phe Leu Glu Lys Phe Asn Lys Ser Lys Arg Glu Arg Leu
            75              80              85

GAG TTG ATG CTG CAT TTT TAT TCT GTG TTA AGT CTT GAA CCT GCT TTT        942
Glu Leu Met Leu His Phe Tyr Ser Val Leu Ser Leu Glu Pro Ala Phe
        90              95              100

GCT GAA CAT TGG TCA GGG GAA TTT GAG AAG TGG AAA GTG GGC TTT TTT        990
Ala Glu His Trp Ser Gly Glu Phe Glu Lys Trp Lys Val Gly Phe Phe
    105             110             115

CAC CCT TTG AAA AGA GAG GAT GGA TTC TTC ACC AGA ACT GAC ATT TAAAAA    1041
His Pro Leu Lys Arg Glu Asp Gly Phe Phe Thr Arg Thr Asp Ile
120             125             130

AAGTCAGCGT GGCACGTTTT AGTATGTGTG GCAGATCTAA AGAGACAATA TTTTGATCTC     1101

AGGAGTGTTT ATTCTTGAAC CATTTTCAGA ACTCTAAGAT TTGAGAAATA ATAAAATATT     1161

GACCATCCTT CAAAGAGAAA AACACAGGGC GATCTTTGGC ATAGCCTGTC ATTTTGCTCA     1221

CATTTCACTT CTCTCTCTCC AACTTCAGAG CCCCTGCTGT GGAACAGGTG CTGTGCTGGG     1281

TGGCAGGGGA GGTCTCTGGC TTTTTTTTTT TGATCTCCGT CTTAACATCT AGCCTACTGG     1341

AGGAAGTGTA TTTAATCATC CACTTATCTG TTAACAATTA TCTCTGAGGG CCCGTCACAT     1401

TCAGAGAAGA TTCTAGGTTC TCTACAAGTA TCCTCTCACT GTGTACATAC TAAATCAACA     1461

TCCTGCTGGA TTTCCCCCAG ACATCTCCCT TCATCACCAT GGAGAGTAT CCTCTAATTG      1521

CCAGCCCTAT TCACCATACT CATCTCATTT GATCTGGAGT TTTCTGAGAG TGACCGGGGG     1581

TGGGATGGAC AGGATAATTT AGCAAGAGTG TATAAGTAAA ATCTATATAA TAAAAGTTAT     1641

CTCCCTGTGC CCCCCATGAT CTATTCTTTA TGTAGCAGTC TGAATGAGAT TTTCAGAAAC     1701

AAGAACCACT TTACCTTAGT CTCTTCTTCT TCTTCTTCTT CTTTTCTTTT CTTTTTTTTT     1761

AGTATTATGG GGATCTGTTT CTGTTGCCCA GGGTGGAGTG CAGTGGTATG ATCTTGGCTC     1821

ACAGCAGCCT TGAACTCCCG GGCTCAAGTG GTCCTCCTGC CTCTGCTTCC CTAGTAGCTA    1881
```

```
GGACTGCAGG TTTGTGCCAC CACACCTGGC TAATTGAAAA AGAAATTTTT TTTTCAATAG    1941

AGACAGTGTC TTGCTATGTC CCCAGGCTGG TCTCAAACTC CTGGCCTCAA GTGATCCTCC    2001

TGTCTCATCC TCCCAAAGTG TTGGAATTAC AGGTGTGAGC TACTATACTC GGCCAGTACC    2061

CTTCTCAAAA CACTTCAGCA CTTCCCATTG CACTTGGGTT GAAATTCCCA CCACTCACTG    2121

GGGCCCACAA GACTCTTCAA GACTGAATCC TTGCTCAACA TTGTGACCTG CCCCCTACCA    2181

CCTGCAGCCT CACTTGCTGT GCTCCAGCCA TGTGGATCTT CCTCCTGTCT CTAAAACTGC    2241

CTCAGGTCAT TTGCACCTGC TGTTCTTCCC AAAGGCTGTG TGATTTCCAT CAGTCAGTCT    2301

TAGCTCGTAT ACCTCCTTGG AGACACCTCT TCTGACCAAC CAGTCCAAAG AATCTCCTCT    2361

TATCATGTCA CTCTGTTTTA TTTATTTATT TAGAGATGGA GTCTCGCTCT GTCACCCAGG    2421

CTGGAGTGCA GTGGCGCGAT CTCTGCTCAC TGCAAGCTCC ACCTCCTGGG TTCATGCCGT    2481

TCTCCTGCCT CAGCCTCCTG AGTAACTGGG ACTATGGGCA CCCACCACTA CACCCGGCTA    2541

ATTTTTTGTA TTTTTAGTGG GGATGGGGTT TCACTGTGTT AGCCAGGATG GTCTTGATCT    2601

CCTGACCTTG TGATCTGCCT GCCTCCACCT CCCAAAGTGT TTTATTTATT TTAAAGGCAT    2661

GTATCACTCT CTGAAAATTA GCTTCTTTCT TCTTTTTCCT TGTTATCATC CATTTCCCCG    2721

AACCAGAATA GAAGTTCCTG AGGCCAGAAC TTCTGTCTCT CTGCCCCTCA CTATGTGTCT    2781

CTGGCACATA CCCCAGTGCC TGCCTGCTCT AAAGTAAAAT CTTAGTAAAT ATTACTGTTG    2841

ACTAAATAAA TGAATAAATC CCTTTTAATG CCCCTTTGGA AGTTGCCAAG TAAAGAATAG    2901

GATCCCTTTT TAAGATTACA CTTTTGGCTA TTGATCTGTG TGTCTGGAAC AAGATACAGT    2961

TTGAAGATAC TACCATGGGA CATGACATCA GTTGAGCTGA TTAAGGTTTT AGTAATAAGA    3021

ATCCAGGATG TGTCCGGGTG CGGTGCTCAC GCCTGTAATC CTAGCATTTT GGGAGACCGA    3081

GGCGGGCAGA TCACGAGGTC AGCAGTTTGA GACCAGCCTG ACCAACATGG TGAAACCCCG    3141

TCTCTACTAA AAAATACAGA AATTAGCCGG GTGTGGTGGT GTCCACCTGT AGTCCTAGCT    3201

ACTCAGGAGG CTGGGGCAGG AGAATTTCTT GAACCCGGGA GGCGGAGGTT GCAGTGAGCC    3261

GAGATCACAC CAGTGCACTC CAGCCTGGGC AACAGAGCAA GACCCAGTCT CAGGAAAAAA    3321

AAAAAAAA                                                             3329

(2) INFORMATION FOR SEQ ID NO:6:

(i) SEQUENCE CHARACTERISTICS:
        (A) LENGTH: 2276 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:6:

CTGAACTGGG AGTCAGGTGG TTGACTTGTG CCTGGCTGCA GTAGCAGCGG CATCTCCCTT     60

GCACAGTTCT CCTCCTCGGC CTGCCCAAGA GTCCACCAGG CC ATG GAC GCA GTG      114
                                               Met Asp Ala Val
                                                1

GCT GTG TAT CAT GGC AAA ATC AGC AGG GAA ACC GGC GAG AAG CTC CTG      162
Ala Val Tyr His Gly Lys Ile Ser Arg Glu Thr Gly Glu Lys Leu Leu
 5                  10                  15                  20

CTT GCC ACT GGG CTG GAT GGC AGC TAT TTG CTG AGG GAC AGC GAG AGC      210
Leu Ala Thr Gly Leu Asp Gly Ser Tyr Leu Leu Arg Asp Ser Glu Ser
```

```
            25                  30                  35
GTG CCA GGC GTG TAC TGC CTA TGT GTG CTG TAT CAC GGT TAC ATT TAT        258
Val Pro Gly Val Tyr Cys Leu Cys Val Leu Tyr His Gly Tyr Ile Tyr
            40                  45                  50

ACA TAC CGA GTG TCC CAG ACA GAA ACA GGT TCT TGG AGT GCT GAG ACA        306
Thr Tyr Arg Val Ser Gln Thr Glu Thr Gly Ser Trp Ser Ala Glu Thr
        55                  60                  65

GCA CCT GGG GTA CAT AAA AGA TAT TTC CGG AAA ATA AAA AAT CTC ATT        354
Ala Pro Gly Val His Lys Arg Tyr Phe Arg Lys Ile Lys Asn Leu Ile
        70                  75                  80

TCA GCA TTT CAG AAG CCA GAT CAA GGC ATT GTA ATA CCT CTG CAG TAT        402
Ser Ala Phe Gln Lys Pro Asp Gln Gly Ile Val Ile Pro Leu Gln Tyr
85              90                  95                 100

CCA GTT GAG AAG AAG TCC TCA GCT AGA AGT ACA CAA GGT ACT ACA GGG        450
Pro Val Glu Lys Lys Ser Ser Ala Arg Ser Thr Gln Gly Thr Thr Gly
                105                 110                 115

ATA AGA GAA GAT CCT GAT GTC TGC CTG AAA GCC CCA TGAAGAAAAA            496
Ile Arg Glu Asp Pro Asp Val Cys Leu Lys Ala Pro
                120                 125

TAAAACACCT TGTACTTTAT TTTCTATAAT TTAAATATAT GCTAAGTCTT ATATATTGTA      556

GATAATACAG TTCGGTGAGC TACAAATGCA TTTCTAAAGC CATTGTAGTC CTGTAATGGA      616

AGCATCTAGC ATGTCGTCAA AGCTGAAATG GACTTTTGTA CATAGTGAGG AGCTTTGAAA      676

CGAGGATTGG GAAAAGTAAT TCCGTAGGTT ATTTTCAGTT ATTATATTTA CAAATGGGAA      736

ACAAAAGGAT AATGAATACT TTATAAAGGA TTAATGTCAA TTCTTGCCAA ATATAAATAA      796

AAATAATCCT CAGTTTTTGT GAAAAGCTCC ATTTTTAGTG AAATATTATT TTATAGCTAC      856

TAATTTTAAA ATGTCTTGCT TGATTGTATG GTGGGAAGTT GGCTGGTGTC CCTTGTCTTT      916

GCCAAGTTCT CCACTAGCTA TGGTGTCATA GGCTCTTTTG GGATTTTGA AGCTGTATAC      976

TGTGTGCTAA ACAAGCACT AAACAAAGAG TGAAGGATTT ATGTTTAATT CTGAAAGCAA      1036

CCTTCTTGCC TAGTGTTCTG ATATTGGACA GTAAAATCCA CAGACCAACC TGGAGTTGAA      1096

AATCTTATAA TTTAAAATAT GCTCTAAACA TGTTTATCGT ATTTGATGCT ACAGGATTTG      1156

AAATTGTATT ACAAATCCAA TGAAATGAGT TTTTCTTTTC ATTTACCTCT GCCCCAGTTG      1216

TTTCTACTAC ATGGAAGACC TCATTTTGAA GGGAAATTTC AGCAGCTGCA GCTCATGAGT      1276

AACTGATTTG TAACAAGCCT CCTTTTAAAG TAACCCTACA AAACCACTGG AAAGTTTATG      1336

GTTGTATTAT TTTTTAAAAA AATTCCAAGT GATTGAAACT TACACGAGAT ACAGAATTTT      1396

ATGCGGCATT TTCTTCTCAC ATTTATATTT TTGTGATTTT GTGATTGATT ATATGTCACT      1456

TTGCTACAGG GCTCACAGAA TTCATTCACT CAACAAACAT AATAGGGCGC TGAGGGCATA      1516

GAAGTAAAAA CACCTGGTCC CTGCTCTCAG TTCACTGTCT TGTTGGACGA GAAAACAATA      1576

ACGATAAAAG ACAGTGAAAG AAAATAACGA TAAAAGACAG TGAAAGAAAA TAACAATAAA      1636

AGACAAGGAA AAAATAACAA TGAAAGTTGA TAAGTACATG ATAAGCGAGG TTCCCCGTGT      1696

GTAGGTAGAT CTGGTCTTTA GAGGCAGATA GATAGGTCAG TGCAAATACT CTGGTCCATG      1756

GGCCATATGA AAAGGCTAAG CTTCACTGTA AAATAATAAC TGGGAATTCT GGGTTGTGTA      1816

TGGGTGTTGG TGAACTTGGT TTTAATTAGT GAACTGCTGA GAGACAGAGC TATTCTCCAT      1876

GTACTGGCAA GACCTGATTT CTGAGCATTT AATATGGATG CCGTGGGAGT ACAAAAGTGG      1936

AGTGTGGCCT GAGTAATGCA TTATGGGTGG TTTACCATTT CTTGAGGTAA AGCATCACA      1996

TGAACTTGTA AAGGAATTTA AAAATCCTAC TTTCATAATA AGTTGCATAG GTTTAATAAT      2056

TTTTAATTAT ATGGCTTGAG TTTAAATTGT AATAGGCGTA ACTAATTTTA ACTCTATAAT      2116
```

```
GTGTTCATTC TGGAATAATC CTAAACATAT GAATTATGTT TGCATGTTCA CTTCCAAGAG    2176

CCTTTTTTTG AAAAAAAGCT TTTTTTGAAT CATCAAGTCT TTCACATTTA AATAAAGTGT    2236

TTGAAAGCTT TATTTAAAAA AAAAAAAAAA AAAAAAAAA                           2276

(2) INFORMATION FOR SEQ ID NO:7:

(i) SEQUENCE CHARACTERISTICS:
         (A) LENGTH: 155 base pairs
         (B) TYPE: nucleic acid
         (C) STRANDEDNESS: double
         (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:7:

CACTTATAAA ATGTTAGGGC TTAATATTAT TCATAGATCG AGGATAGTTT CATTCTTAGT     60

CGCCTCCTTA GTCACTCTTC CTATACCAAT CTGAGACCAT TTTACAATTT AGAAAGACA    120

AATAACTGGT TGGGTTACTT GATAGTATAA TAACC                              155

(2) INFORMATION FOR SEQ ID NO:8:

(i) SEQUENCE CHARACTERISTICS:
         (A) LENGTH: 278 base pairs
         (B) TYPE: nucleic acid
         (C) STRANDEDNESS: double
         (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:8:

GAAGGAGAAT ATGAAGAGGT TAGAAAAGNT CNGGNTTCTG TTGGTGAAAT GAAGGATGAA     60

GGGGAAGAGA CATTAAATTA TCCTGATACT ACCATTGACT TGTCTCACCT TCAACCCCAA    120

AGGTCCATCC AGAAATTGGC TTCAAAAGAG GAATCTTCTA ATTCTAGTGA CAGTAAATCA    180

CAGAGCCGGA GACATTTGTC AGCCAAGGAA AGAAGGGAAA TGAAAAAGAA AAAACTTCCA    240

AGTGACTCAG GAGATTTAGA AGCGTTAGAG GGAAAGGA                           278

(2) INFORMATION FOR SEQ ID NO:9:

(i) SEQUENCE CHARACTERISTICS:
         (A) LENGTH: 135 base pairs
         (B) TYPE: nucleic acid
         (C) STRANDEDNESS: double
         (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:9:

TTCTGACAAT GAGTAAGAAG AAAGAGGGTC TTGCCCTTTG GTTATTAAGA TTTATCATAG     60

AGCAATAATA ASTAAATCGG TGTTATACCA GCACAGAGAT TAGACAAATA AACCAAGGGA    120

CTGGACTAAA TAAGC                                                    135
```

(2) INFORMATION FOR SEQ ID NO:10:

(i) SEQUENCE CHARACTERISTICS:
        (A) LENGTH: 197 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:10:

```
ATGGTACCCA GTTTCAAATT AACATGGTTA TTTTACTTGT GTTCCCAAAT TTAACATTAG    60

GGAATTTTTG GTTGTGGGTC TGTTATCACT AGAAAAATAT ATATATTGGT GCTGAAGATA   120

ATTTTGAGAT AATTAGACAA GACAGTTTAG CATTTACAAG AACAAGTTTG GCAGTTGAAG   180

AATCTATTTA TATGACT                                                  197
```

(2) INFORMATION FOR SEQ ID NO:11:

(i) SEQUENCE CHARACTERISTICS:
        (A) LENGTH: 137 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:11:

```
CCACCGCACC TGGCTGATGC TTTTCTATCT GACTTCTTTC AGAGGACCCT GAAAGACACT    60

AAGTGGAATC TTTCCTTGAA GTCTTCCAAG CTAAAACAAT TCTCTGGAAA GATCACCTCT   120

GTTCAGTCCT GGTCTCT                                                  137
```

(2) INFORMATION FOR SEQ ID NO:12:

(i) SEQUENCE CHARACTERISTICS:
        (A) LENGTH: 274 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:12:

```
CGTTTACAGA TTCTCTTGCG GCTGGCGGTG GAACTACAAA GGGATCGGTG CCTATATCAC    60

AATACCAAAC TTGATAATAA TCTAGATTCT GTGTYTCTGC TTATAGACCA TGTTTGTAGT   120

AGGTAAGAGG AAAACTTCCT ATATTCTGAA ACAGCCTAAC ATTTTACAAA ATTTTAGTTT   180

TCTTTTTTAG AGTCTTATCC TGTAGCTATA TAACAGTTCA TGTCTGATTT AGCATTTGTT   240

CACGAGTAAA GCTGGAACTA TGAAAATTGA AAAT                               274
```

(2) INFORMATION FOR SEQ ID NO:13:

(i) SEQUENCE CHARACTERISTICS:
    (A) LENGTH: 171 base pairs
    (B) TYPE: nucleic acid
    (C) STRANDEDNESS: double
    (D) TOPOLOGY: linear (ii) MOLECULE TYPE: cDNA (vi) ORIGINAL SOURCE:
    (A) ORGANISM: human
    (G) CELL TYPE: leukocyte (xi) SEQUENCE DESCRIPTION: SEQ ID NO:13:

GATTAGGTGA CCTTCCTTGA ARAGCCACGG GTTTCCCATA TCGAAATGCT ATTCATTACC      60

CGAGTCACCT ANGTTCTTAC AAAGGAAGCG AGAAAATTGC TTTTGTTGGG CCATGCCCCT    120

TTTGCANAGG TTCCTAAGTA TAGTCGCCAN AATTTTTTA ATGGCCTAAA G              171

(2) INFORMATION FOR SEQ ID NO:14:

(i) SEQUENCE CHARACTERISTICS:
        (A) LENGTH: 161 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:14:

AGGGGCGCTT GTTCTGCTCT CAGCAGATTG GTTACACGCG TCAGGTGGTG GCGATGACTT     60

AATTCCTAGC CCAAGAAGAA TATAATGTTA AAACTGGTTA TGTAATTTTT GTGCCTCTCC    120

TTTTTAATGC AGTATTTAGT TCAGATGTTG GCGATTTTTC A                        161

(2) INFORMATION FOR SEQ ID NO:15:

(i) SEQUENCE CHARACTERISTICS:
        (A) LENGTH: 323 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:15:

TATAAGGWGG GAACCTTACT ATCTCTAATG ACCTTACTGA TGCTGACTTT AATACTCTGT     60

GAAGGTTAGA GTTCAGTGAA TGTTACCTAG AAACAGCCCC GGCTGTGGAA TACTTTATTC    120

TTAGCCCTAT ATTTGGGGTT TGGATGTCCA CTGTGCTGGT TCCCAGAGAT AGTAAGGGGA    180

TGAGAGTATT GGTTACATCT CCTGACCCAC ATACTTAAGA TCCAGATGAA CAAGACAGTT    240

TTCACTCCTG CTTGGTAGAA CCTATTTGYK SHAGGAAACA GYTCCTAAAG AATGGTTCTA    300

GCCAGACCCT GTCGYTACCA GAA                                            323

(2) INFORMATION FOR SEQ ID NO:16:

(i) SEQUENCE CHARACTERISTICS:
        (A) LENGTH: 138 base pairs
        (B) TYPE: nucleic acid
        (C) STRANDEDNESS: double (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:16:

AGTATGACAA ATAGTTTCTG CCTGATTGGT GAGATTTGGG ATGGGCCCCC ACTTTGTTTC     60

TCTTTCTGCA TAAAAATTTC AACATTTTTA CAAAATTTTC AAAAACTTCT CCTCAGTCTG    120

TACATCTTTG TTAATCAG                                                  138

(2) INFORMATION FOR SEQ ID NO:17:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:17:

TGATCCCCAC AATTTCTTGT GATTGGTGAG GAACTATAAA TGACTCCCAT CCAAGCTTAT     60

ACCAGAAAAA AGGAGCACAT TTTCTACAAA TTATATCATT TTTAATCCAT TACCACATTA    120

TTTTAGGGGA ACTAC                                                     135

(2) INFORMATION FOR SEQ ID NO:18:

(i) SEQUENCE CHARACTERISTICS:
        (A) LENGTH: 219 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:18:

CTGAGAGGAG CCATGTATAC AAACCACTTT TTCTAACATG GTCTTTATTA AACTTTGAAT     60

ATAAGTACAC CTGCTCGAAG TGTTCATCTA TATTATTTAA GAACAAGCAA CTGTAAAACA    120

GTAAAATCAC AAAAGGTAAG TTGTTGGAAG ACAACAAAAA AGAATTACTA TATCTGATCC    180

TGCGTGTTTA TTTTAGAATC TGTTAATAGG CCTACAGCT                           219

(2) INFORMATION FOR SEQ ID NO:19:

(i) SEQUENCE CHARACTERISTICS:
        (A) LENGTH: 191 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:19:

ACAGTGAGTG TGGCTGAAAC CTAAGCTGAA GGAAGGGAGG AGCAGGCACT GCCATGAGGG    60

GTCCCTGGAC AGAAACTCTT CAGCAGGCCT TGAAGTTTAG TTCAGGGGCT ACATGGAATA    120

CCACTATTTA GCACACAGGT GTGATCTGAG GTGAGGGACT ACCTTTTCGA TCTTGGTTTT    180

CTCATTTATT T    191

(2) INFORMATION FOR SEQ ID NO:20:

(i) SEQUENCE CHARACTERISTICS:
        (A) LENGTH: 148 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:20:

CTGGAGGTGA AGGGAAGGAA AGAAAGGAAA AACTATCTAC CTGGCAGGAA AAGAGATAAG    60

CTCCCAAGAA CACCAAAGCA GATGATGAGT CTAGCTCTAC CCAGCCTTCC TCCCCACGAA    120

TCCAGATCAT AGTAAGAAAC TCTGGGCT    148

(2) INFORMATION FOR SEQ ID NO:21:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:21:

CCACCACCAG AAATGAACAA AAAGCATTTT ACCTAAAAAT ACACCAGCAA AATGTACTCA    60

GCTTCAATCA CAAATACGAC TGCTTAAAAC CGCAGAAATT TCCTCAACAC TCAGCCTTTA    120

TCACTCAGCT GGATTTTTTC CTTCAACAAT CACTACTCCA AGCATTGGGG AACACAACTT    180

TTAATCATAC TCCAGTCGTT TCACAATGCA TTCTAATAGC AGCGGATCA GAACAGTACT    240

GCATTTACTT GCCAACAGAA CAGACAGACC TGAAGTCAAG ACAACTGCAT TCTCTGTGAA    300

GTCTGT    306

(2) INFORMATION FOR SEQ ID NO:22:

(i) SEQUENCE CHARACTERISTICS:
        (A) LENGTH: 357 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:22:

```
GTAGCATTTT GGCAGAACCA TTGTTAATTA AAGGGACTTY TGGACCGCAA CYTTAATGTA        60

CCAGATTATT GAGCRGCCCA ATGAATGCTT CATTCTCATT GTTTAAGGTG CTGCTTTGAT       120

TTTTTTTTCA ATTCTTTGTA CTATTTTTTA TTTTTTGGAG AGGCACATCC CCAAATTTGG       180

ATGAGGTATT TGTTGATAAA TAATTCATCA ATTTCCACAA TGCAGACAAA AATGTCTGCC       240

CAGAGTGGAA AAATAAAACA AGGGGGAGAA GAGTTTGAGT AACGGAGAAG TTCTGTGGAA       300

TCCTAGTGAC AAAAGTTGAG AAACTACCTT TAAATAAGAC AGTGAGGTAA CAAATGT         357
```

(2) INFORMATION FOR SEQ ID NO:23:

(i) SEQUENCE CHARACTERISTICS:
        (A) LENGTH: 219 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:23:

```
TGGAATAGCC AGGAGAATTC TGGAAAAGTA GAATAATGAG GTAGGGCTTC CCTTCGCTAT        60

TTTGAAGTGC AGATTACACT ATGTAAAACC ATTAGGAACT GGCACGTGAA TAGACAGATC       120

AATAGTTAAT AGCTGTATTA GCCAGAAAAT GGTGTAAGGA CAACAGGCTA ACTAACCCTG       180

TCACTTGTTA TGCTAAAATT AAGTCTAGAT AGAGTCCTC                             219
```

(2) INFORMATION FOR SEQ ID NO:24:

(i) SEQUENCE CHARACTERISTICS:
        (A) LENGTH: 251 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:24:

```
TGAAAGGGGA ATAGAAGCAC AAGAGTCAGT AATCAATAAC AAACAACTCA AGGTGCTCCT        60

TCCTTACACT GGTGTTCCCC AAAGTGAGGT GAATTGCCAG CCACTGGGAG TCAGGGCCAG       120

TTACATAAGA CATTCTCGGT AAGCCCCCTT TGGGTATCCC AAATAAGGAC TGGGGTGGGT       180

TTATGTGTAG TCCATTATTA ACAACTAAAC GAACAAACCT AGTGAATTGC AATAAATTCA       240

CACCAACAGA A                                                          251
```

(2) INFORMATION FOR SEQ ID NO:25:

(i) SEQUENCE CHARACTERISTICS:
        (A) LENGTH: 233 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:25:

GTTGAAAGAG TCCTTGGAAG GCTTTTAGAC CAAACCCCTC TGCATGCTCA ARCCTTGGGT     60

ACAGGATTTC TAAGAAGTGG AACAGTCTCC AGGGGTGTGG ARCTCATCGC TCAAGGCAGG    120

TTATCTTATC TGAATAATTT TGTCTGTTGA CTATTGGGAT AGTTCTCCTT CAGATGAGCT    180

GAAATTTTCT CCATAGCTTC CTCTATTAAA CCCAATTCCA CTTCTCAGGG TCA           233

(2) INFORMATION FOR SEQ ID NO:26:

(i) SEQUENCE CHARACTERISTICS:
        (A) LENGTH: 176 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:26:

CAAAAGCGCT GAAGTTAAGC ATTAATACGC CAGATTCATG ATTTATGATC AGTATCCAAA     60

ACTCCAACTA CAAACAATGC AAAGTAGTGC TCCTCAGTAT TATTTTTGCA ATTGTTAGTA    120

ATGTTAAGCA TCAAGGAAAA TAAAACACAT CATTGCACAT TACAGCCGCA AAAAC         176

(2) INFORMATION FOR SEQ ID NO:27:

(i) SEQUENCE CHARACTERISTICS:
        (A) LENGTH: 241 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:27:

AGAGAGTAAA GCAAGCTATT TTGACAGCAA CCTAATAACA GCTGTCTTCT TCCACTTCTT     60

GGCTAACTCA TCCCCCAGAT AGCCTTCTTT TCTCTTATCA ATTCCCTGTT GCAACAATAA    120

TAAATGCCAC ACCTGATGGA GTCATTAGGC ACTTTCCTAG TGACAAGTGC CTAGGACAGA    180

GGAGAAAACA AAGAAACACT GACAACCACT GAAAACTGAC ATATCAGGCC AGGCATGTCA    240

C                                                                    241

(2) INFORMATION FOR SEQ ID NO:28:

(i) SEQUENCE CHARACTERISTICS:
        (A) LENGTH: 217 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:28:

GCTGGAGAGG TGGTGATGTT GCTGAATAAT TGCTTTTTAA AGCTGGAGGG GACTTCCAAG     60

```
AGTCTCTCAT TTAAGAARAA AAATTAAAGA CATAATTGGT AACGGTTTTG ACTGCTGCAG      120

AGGCAACACT TTGCTCACAA TCCTACAGAT CTACTTCACC TGTAACTACA ATTTTCCTGA      180

AGACATAGAA GAAAAATCAA TTGTTCTAAT CCATATG                              217

(2) INFORMATION FOR SEQ ID NO:29:

(i) SEQUENCE CHARACTERISTICS:
        (A) LENGTH: 233 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:29:

AATCTTAGCA TAATGCTTCC TGGGAAATTC TGAAATTGAT TCCATTTCTG CCGTTACAAA       60

CACACACGAA GTTCCTAGTT CACTGGGACT TCCTGATTTG TTCTTTTAGC TTGCTCCTTC      120

TCACCTAGAA GCTCTGTTTA TTTCTGAGCA ACCCTGGGGC TTGTCTCATA GGACAGGATT     180

TATTTATCTC ATCAAGGCTG AGTGTGCCTT AGGAAGTCAT AAACATAAAA AGA            233

(2) INFORMATION FOR SEQ ID NO:30:

(i) SEQUENCE CHARACTERISTICS:
        (A) LENGTH: 228 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:30:

TATAGACAGG GTAGGGACGA TTAGCCCCTC GACAACTTTT CACAAATATA CACACGTTTA       60

ACTACCTCTC AGGTCATGAT AAAGACCGGC CGGGCAGAAA CACTGTAATC CCAGCTACTC     120

GGGAGCCTGA GGCATGAGAA TCACTTGAAC CTGGGAGGTG GAGGTTGCCA TGAGCCGAGA     180

TCACGCCATT GCACTACAGC CTTGGCGACA AGAGTGAAAC TCCATCTG                  228

(2) INFORMATION FOR SEQ ID NO:31:

(i) SEQUENCE CHARACTERISTICS:
        (A) LENGTH: 298 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
         (A) ORGANISM: human
         (G) CELL TYPE: leukocyte (xi) SEQUENCE DESCRIPTION: SEQ ID NO:31:

GCTTATGATT ACAAACATCC CTCATATGAA AATCTCAGCA TTTNCTGGCT GCTGCCTTCA       60

ATCGCTTTTT CTGAAATAGG TATCCCTTGA TGTCGACTAT TTGATTTCAG CCAGTCGTTT     120

CTCTCTGGCA GTGCTCCCTG CAAATGTGTC CTTTCAAGAA AACAAAACCT GCAAGTGGCT     180
```

```
TGTAATGTAC CATGACCTTA TCATGTGAAG GACAAATGGC TCTTGTGCTT ATTAGATAGC      240

AGATGAACTG ATGAACTGAA TTCTTGGTCT GAAGCTTTGA TAAGGTCAGA TGTCTTTG       298
```

(2) INFORMATION FOR SEQ ID NO:32:

(i) SEQUENCE CHARACTERISTICS:
        (A) LENGTH: 291 base pairs
        (B) TYPE: nucleic acid
        (C) STRANDEDNESS: double
        (D) TOPOLOGY: linear (i) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:32:

```
ACTTCGAAGG GAAAAAGAGG AAGGAAAAGG ACTGTTAATA AAATAACAAA GGCAGCAATC       60

AGAATGAACC AGAGCCAGGA CAGCGTAAAG GCTAGGTTCA CAGTGAGATG AAAGAACCTG      120

AAAACAAGTT TAAAACTCAA AAGAGGATTA TTCTCAAGTT ATACTACAGT GAAAAAACAT      180

GGAAAAACAC AAAAAGGACA GGCAATAAGG CACAGGCATA CATACAAGGC AAATTGTAAC      240

ACAATATTTA CTTGCAAAAG AGCCCACAGA GACATGTCAA TGAAGTCATA G               291
```

(2) INFORMATION FOR SEQ ID NO:33:

(i) SEQUENCE CHARACTERISTICS:
        (A) LENGTH: 230 amino acids
        (B) TYPE: amino acid
        (D) TOPOLOGY: linear (ii) MOLECULE TYPE: protein (vi) ORIGINAL SOURCE:
        (A) ORGANISM: human
        (G) CELL TYPE: leukocyte (xi) SEQUENCE DESCRIPTION: SEQ ID NO:33:

```
Met Glu Asp Gly Phe Leu Asp Asp Gly Arg Gly Asp Gln Pro Leu His
  1               5                  10                  15

Ser Gly Leu Gly Ser Pro His Cys Phe Ser His Gln Asn Gly Glu Arg
             20                  25                  30

Val Glu Arg Tyr Ser Arg Lys Val Phe Val Gly Gly Leu Pro Pro Asp
         35                  40                  45

Ile Asp Glu Asp Glu Ile Thr Ala Ser Phe Arg Arg Phe Gly Pro Leu
 50                  55                  60

Ile Val Asp Trp Pro His Lys Ala Glu Ser Lys Ser Tyr Phe Pro Pro
 65                  70                  75                  80

Lys Gly Tyr Ala Phe Leu Leu Phe Gln Asp Glu Ser Ser Val Gln Ala
             85                  90                  95

Leu Ile Asp Ala Cys Ile Glu Glu Asp Gly Lys Leu Tyr Leu Cys Val
            100                 105                 110

Ser Ser Pro Thr Ile Lys Asp Lys Pro Val Gln Ile Arg Pro Trp Asn
            115                 120                 125

Leu Ser Asp Ser Asp Phe Val Met Asp Gly Ser Gln Pro Leu Asp Pro
130                 135                 140

Arg Lys Thr Ile Phe Val Gly Val Pro Arg Pro Leu Arg Ala Val
145                 150                 155                 160

Glu Leu Ala Met Val Met Asp Arg Leu Tyr Gly Val Cys Tyr Ala
            165                 170                 175
```

```
Gly Ile Asp Thr Asp Pro Glu Leu Lys Tyr Pro Lys Gly Ala Gly Arg
            180                 185                 190

Val Ala Phe Ser Asn Gln Gln Ser Tyr Ile Ala Ala Ile Ser Ala Arg
        195                 200                 205

Phe Val Gln Leu Gln His Gly Glu Ile Asp Lys Arg Val Ser Leu Ile
    210                 215                 220

Leu His Phe Gly Lys Phe
225                 230

(2) INFORMATION FOR SEQ ID NO:34:

(i) SEQUENCE CHARACTERISTICS:
        (A) LENGTH: 143 amino acids
        (B) TYPE: amino acid
        (D) TOPOLOGY: linear (ii) MOLECULE TYPE: protein (vi) ORIGINAL SOURCE:
        (A) ORGANISM: human
        (G) CELL TYPE: leukocyte (xi) SEQUENCE DESCRIPTION: SEQ ID NO:34:

Met Gly Ser Asp Lys Arg Val Ser Arg Thr Glu Arg Ser Gly Arg Tyr
1               5                   10                  15

Gly Ser Ile Ile Asp Arg Asp Arg Asp Glu Arg Glu Ser Arg Ser
            20                  25                  30

Arg Arg Arg Asp Ser Asp Tyr Lys Arg Ser Ser Asp Asp Arg Arg Gly
        35                  40                  45

Asp Arg Tyr Asp Asp Tyr Arg Asp Tyr Asp Ser Pro Glu Arg Glu Arg
    50                  55                  60

Glu Arg Arg Asn Ser Asp Arg Ser Glu Asp Gly Tyr His Ser Asp Gly
65                  70                  75                  80

Asp Tyr Gly Glu His Asp Tyr Arg His Asp Ile Ser Asp Glu Arg Glu
                85                  90                  95

Ser Lys Thr Ile Met Leu Arg Gly Leu Pro Ile Thr Ile Thr Glu Ser
            100                 105                 110

Asp Ile Arg Glu Met Met Glu Ser Phe Glu Gly Pro Gln Pro Ala Asp
        115                 120                 125

Val Arg Leu Met Lys Arg Lys Thr Gly Glu Ser Leu Leu Ser Ser
    130                 135                 140     143

(2) INFORMATION FOR SEQ ID NO:35:

(i) SEQUENCE CHARACTERISTICS:
        (A) LENGTH: 104 amino acids
        (B) TYPE: amino acid
        (D) TOPOLOGY: linear (ii) MOLECULE TYPE: protein (vi) ORIGINAL SOURCE:
        (A) ORGANISM: human
        (B) CELL TYPE: leukocyte (xi) SEQUENCE DESCRIPTION: SEQ ID NO:35:

Met Pro His Met Leu Ser Gln Leu Ile Ala Gly Gly Val Ser Thr Ser
1               5                   10                  15

Cys Val Thr Ala Leu Gly Glu Glu Thr Gly Ala Trp Phe Pro Val Tyr
            20                  25                  30

Leu Ser His Ala Ser Ser Pro Phe Ala Asp Leu Val Phe Cys Pro Phe
```

```
                35              40              45
Ala Glu Ile Asn His Ser Gln Glu Tyr Asp Asn Met Arg Gly Pro Val
 50                  55                  60

Ser Pro Pro Asn Lys Gln Phe Asn Leu Gly Val Ile Phe Gly Ile Pro
 65                  70                  75                  80

Asn Asn Cys Arg Phe Pro Thr Asp Asn Lys Ile Thr Glu Lys Gln Leu
                 85                  90                  95

Leu Gly Asn Val Leu Asn Tyr Pro
                100
```

(2) INFORMATION FOR SEQ ID NO:36:

(i) SEQUENCE CHARACTERISTICS:
        (A) LENGTH: 133 amino acids
        (B) TYPE: amino acid
        (D) TOPOLOGY: linear (ii) MOLECULE TYPE: protein (vi) ORIGINAL SOURCE:
        (A) ORGANISM: human
        (G) CELL TYPE: leukocyte (xi) SEQUENCE DESCRIPTION: SEQ ID NO:36:

```
Met Asn His Pro Trp His Val Cys Phe Leu Phe Lys Val Leu Arg Tyr
 1               5                  10                  15

Tyr Pro Thr Ala Pro Ile Leu Lys Trp Thr His Thr Val Ser Cys Ser
                 20                  25                  30

Trp Cys Arg Ser Val Leu Arg Glu Val Val Gly Asn Val Ser Leu Ser
                 35                  40                  45

Glu Asn Phe Thr Ile Ser Ala Phe Cys Pro Glu Leu Thr Pro Phe Pro
 50                  55                  60

Asp Gln Gly Thr Ser Thr Met Ile Ser Phe Leu Glu Lys Phe Asn Lys
 65                  70                  75                  80

Ser Lys Arg Glu Arg Leu Glu Leu Met Leu His Phe Tyr Ser Val Leu
                 85                  90                  95

Ser Leu Glu Pro Ala Val Ala Glu His Trp Ser Gly Glu Phe Glu Lys
                100                 105                 110

Trp Lys Val Gly Phe Phe His Pro Leu Lys Arg Glu Asp Gly Phe Phe
                115                 120                 125

Thr Arg Thr Asp Ile
                130
```

(2) INFORMATION FOR SEQ ID NO:37:

(i) SEQUENCE CHARACTERISTICS:
        (A) LENGTH: 133 amino acids
        (B) TYPE: amino acid
        (D) TOPOLOGY: linear (ii) MOLECULE TYPE: protein (vi) ORIGINAL SOURCE:
        (A) ORGANISM: human
        (G) CELL TYPE: leukocyte (xi) SEQUENCE DESCRIPTION: SEQ ID NO:37:

```
Met Asn His Pro Trp His Val Cys Phe Leu Phe Lys Val Leu Arg Tyr
 1               5                  10                  15

Tyr Pro Thr Ala Pro Ile Leu Lys Trp Thr His Thr Val Ser Cys Ser
                 20                  25                  30
```

```
Trp Cys Arg Ser Val Leu Arg Glu Val Val Gly Asn Val Ser Leu Ser
        35                  40                  45

Glu Asn Phe Thr Ile Ser Ala Phe Cys Pro Glu Leu Thr Pro Phe Pro
    50                  55                  60

Asp Gln Gly Thr Ser Thr Met Ile Ser Phe Leu Glu Lys Phe Asn Lys
65                  70                  75                  80

Ser Lys Arg Glu Arg Leu Glu Leu Met Leu His Phe Tyr Ser Val Leu
                85                  90                  95

Ser Leu Glu Pro Ala Phe Ala Glu His Trp Ser Gly Glu Phe Glu Lys
            100                 105                 110

Trp Lys Val Gly Phe Phe His Pro Leu Lys Arg Glu Asp Gly Phe Phe
        115                 120                 125

Thr Arg Thr Asp Ile
        130
```

(2) INFORMATION FOR SEQ ID NO:38:

(i) SEQUENCE CHARACTERISTICS:
        (A) LENGTH: 128 amino acids
        (B) TYPE: amino acid
        (D) TOPOLOGY: linear (ii) MOLECULE TYPE: protein (vi) ORIGINAL SOURCE:
        (A) ORGANISM: human
        (G) CELL TYPE: leukocyte (xi) SEQUENCE DESCRIPTION: SEQ ID NO:38:

```
Met Asp Ala Val Ala Val Tyr His Gly Lys Ile Ser Arg Glu Thr Gly
1               5                   10                  15

Glu Lys Leu Leu Leu Ala Thr Gly Leu Asp Gly Ser Tyr Leu Leu Arg
            20                  25                  30

Asp Ser Glu Ser Val Pro Gly Val Tyr Cys Leu Cys Val Leu Tyr His
        35                  40                  45

Gly Tyr Ile Tyr Thr Tyr Arg Val Ser Gln Thr Glu Thr Gly Ser Trp
    50                  55                  60

Ser Ala Glu Thr Ala Pro Gly Val His Lys Arg Tyr Phe Arg Lys Ile
65                  70                  75                  80

Lys Asn Leu Ile Ser Ala Phe Gln Lys Pro Asp Gln Gly Ile Val Ile
                85                  90                  95

Pro Leu Gln Tyr Pro Val Glu Lys Lys Ser Ser Ala Arg Ser Thr Gln
            100                 105                 110

Gly Thr Thr Gly Ile Arg Glu Asp Pro Asp Val Cys Leu Lys Ala Pro
        115                 120                 125
```

(2) INFORMATION FOR SEQ ID NO:39:

(i) SEQUENCE CHARACTERISTICS:
        (A) LENGTH: 305 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:39:

```
TCATGAAGTG AAGCCAACTG TTTAGACTAG AATGTTATGA GATTAAACCC ACNNNNNNTT     60
```

```
ATTCATAGAC ATAAACCCTC ATTTTAATTA GTGGATCTGG ATTTTTGTCA TATGTGGAAT      120

CATAATTTAA ACAAAATCAA CTAAGATGAT CCAAGTTCCA CACAACTGCA CTTCAATATT      180

CAAGTCGGTG TGAAGATGCC TGACTACTGC GTCACAAGAT TCTGAGCTGT CGTAAAAAGC      240

CTGGCTCGTG GTTTCTATTT ATAGTGTACA CATGTTGGGT TATAATCACA AACCTGGAAC      300

TCTGT                                                                 305
```

(2) INFORMATION FOR SEQ ID NO:40:

(i) SEQUENCE CHARACTERISTICS:
        (A) LENGTH: 256 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:40:

```
GAAACCACGG CTTACACCTA GAGACAGCAT TCAGATATAG ACGGGATACT TGTGTTAGTC       60

AGTTCCTTTA TAACAGGTGA ATCTCTCTCC CACTGCTTCA ACACTGCGTG ACAAAGCCAA      120

TTGGGAAGCA GCTTTACAAA TGTGACTTGA CTTGGGGATC TTCTTGATAC TTTGCCATGG      180

CAAGGAACAA GCCGCCTGAA CTAAATGCCA CTCCATTTGA TTCCACGCTT AAAGTAACCA      240

TGCAACCGAC TATAGT                                                     256
```

(2) INFORMATION FOR SEQ ID NO:41:

(i) SEQUENCE CHARACTERISTICS:
        (A) LENGTH: 244 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:41:

```
TACTCTTCAA CCATGATTTT CTCTGATGG CCTGTGTGAA CAGATTAATG GTGTCCATCT        60

AATTCCTTCC CCACTGGGGG AAAGCAAATC ATCAGGCCCA TTGCAAAAAC TGCTCTTGGT      120

TGAGCTTCCT GCCTTAAATC ATACCCACAG TGAATGGCGT CCCTTTATCA CCGCTAATGA      180

CTCTGACATC TCTCTCCACT CACATGTGAG CCTCCTCAGC TCTCGANAAA CAAGTCNGTC      240

TCGG                                                                  244
```

(2) INFORMATION FOR SEQ ID NO:42:

(i) SEQUENCE CHARACTERISTICS:
        (A) LENGTH: 258 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (G) CELL TYPE: leukocyte (xi) SEQUENCE DESCRIPTION: SEQ ID NO:42:

TCTCAGAAAA CTCCAGATCA AATGAGATGA GTATGGTGNN NAGGGCTGGC AATTAGAGGA     60

TACTCTCCAA TGGTGATGAA GGGAGATGTC TGGGGGAAAT CCAGCAGGAT GTTGATTTAG    120

TATGTACACA GTGAGAGGAT ACTTGTAGAG AACCTAGAAT CTTCTCTGAA TGTGACGGGC    180

CCTCAGAGAT AATTGTTAAC AGATAAGTGG ATGATTAAAT ACACTTCCTC CAGTAGGCTA    240

GATGTTAAGA CGGAGATC                                                  258

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid; synthetic DNA (xi) SEQUENCE DESCRIPTION: SEQ ID NO:43:

GGGCTTAATA TTATTCATAG ATCGAG                                          26

(2) INFORMATION FOR SEQ ID NO:44:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:44:

GTTATTATAC TATCAAGTAA CCCAAC                                          26

(2) INFORMATION FOR SEQ ID NO:45:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:45:

GTGGATCTGG ATTTTTGTCA TATGT                                           25

(2) INFORMATION FOR SEQ ID NO:46:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:46:

GTTTGTGATT ATAACCCAAC ATGTG                                           25

(2) INFORMATION FOR SEQ ID NO:47:

(i) SEQUENCE CHARACTERISTICS:
        (A) LENGTH: 25 base pairs
        (B) TYPE: nucleic acid

```
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:47:

GAAGGGGAAG AGACATTAAA TTATC                                    25

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:48:

GCTTCTAAAT CTCCTGAGTC ACTT                                     24

(2) INFORMATION FOR SEQ ID NO:49:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:49:

GACAATGAGT AAGAAGAAAG AGGG                                     24

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:50:

GTCCAGTCCC TTGGTTTATT TGTC                                     24

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:51:

GGTACCCAGT TTCAAATTAA CATGG                                    25

(2) INFORMATION FOR SEQ ID NO:52:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA
```

(xi) SEQUENCE DESCRIPTION: SEQ ID NO:52:

GATTCTTCAA CTGCCAAACT TGTTC                                    25

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:53:

GCTGATGCTT TTCTATCTGA CTTC                                     24

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:54:

GACCAGGACT GAACAGAGGT GA                                       22

(2) INFORMATION FOR SEQ ID NO:55:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:55:

GCTTATAGAC CATGTTTGTA GTAGG                                    25

(2) INFORMATION FOR SEQ ID NO:56:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:56:

GTGAACAAAT GCTAAATCAG ACATG                                    25

(2) INFORMATION FOR SEQ ID NO:57:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:57:

GCCACGGGTT TCCCATATCG AA                                       22

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:58:

GACTATACTT AGGAACCTCT GCAA                                    24

(2) INFORMATION FOR SEQ ID NO:59:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:59:

GTTCTGCTCT CAGCAGATTG GTTA                                    24

(2) INFORMATION FOR SEQ ID NO:60:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:60:

GCCAACATCT GAACTAAATA CTGC                                    24

(2) INFORMATION FOR SEQ ID NO:61:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:61:

GTTCAGTGAA TGTTACCTAG AAACA                                  25

(2) INFORMATION FOR SEQ ID NO:62:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:62:

GGAGTGAAAA CTGTCTTGTT CATC                                    24

(2) INFORMATION FOR SEQ ID NO:63:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid, synthetic DNA (xi) SEQUENCE DESCRIPTION: SEQ ID NO:63:

GTATGACAAA TAGTTTCTGC CTGAT                                  25

(2) INFORMATION FOR SEQ ID NO:64:

(i) SEQUENCE CHARACTERISTICS:
       (A) LENGTH: 25 base pairs
       (B) TYPE: nucleic acid
       (C) STRANDEDNESS: single
       (D) TOPOLOGY: linear (ii) MOLECULE TYPE: other nucleic acid, synthetic DNA (xi) SEQUENCE DESCRIPTION: SEQ ID NO:64:

GATTAACAAA GATGTACAGA CTGAG                                  25

(2) INFORMATION FOR SEQ ID NO:65:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid, synthetic DNA (xi) SEQUENCE DESCRIPTION: SEQ ID NO:65:

GAGACAGCAT TCAGATATAG ACGG                                   24

(2) INFORMATION FOR SEQ ID NO:66:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: other nucleic acid, synthetic DNA (xi) SEQUENCE DESCRIPTION: SEQ ID NO:66:

GCGTGGAATC AAATGGAGTG GC                                     22

(2) INFORMATION FOR SEQ ID NO:67:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: other nucleic acid, synthetic DNA (xi) SEQUENCE DESCRIPTION: SEQ ID NO:67:

GATGGCCTGT GTGAACAGAT TAAT                                   24

(2) INFORMATION FOR SEQ ID NO:68:

(i) SEQUENCE CHARACTERISTICS:
       (A) LENGTH: 24 base pairs
       (B) TYPE: nucleic acid
       (C) STRANDEDNESS: single (D) TOPOLOGY: linear (ii) MOLECULE TYPE: other nucleic acid, synthetic DNA (xi) SEQUENCE DESCRIPTION: SEQ ID NO:68:

GAGAGAGATG TCAGAGTCAT TAGC                                          24

(2) INFORMATION FOR SEQ ID NO:69:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:69:

GATCCCCACA ATTTCTTGTG ATTG                                          24

(2) INFORMATION FOR SEQ ID NO:70:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:70:

GTTCCCCTAA AATAATGTGG TAATG                                         25

(2) INFORMATION FOR SEQ ID NO:71:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:71:

GAGGATACTC TCCAATGGTG ATG                                           23

(2) INFORMATION FOR SEQ ID NO:72:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:72:

GTCTTAACAT CTAGCCTACT GGAG                                          24

(2) INFORMATION FOR SEQ ID NO:73:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:73:

GAGAGGAGCC ATGTATACAA ACCA                                                     24

(2) INFORMATION FOR SEQ ID NO:74:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:74:

GCACGCAGGA TCAGATATAG TAATTC                                                   26

(2) INFORMATION FOR SEQ ID NO:75:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:75:

GCTGAAACCT AAGCTGAAGG AAGG                                                     24

(2) INFORMATION FOR SEQ ID NO:76:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:76:

GTCCCTCACC TCAGATCACA CC                                                       22

(2) INFORMATION FOR SEQ ID NO:77:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:77:

GCTATCTACC TGGCAGGAAA AGAG                                                     24

(2) INFORMATION FOR SEQ ID NO:78:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:78:

GAGTTTCTTA CTATGATCTG GATTC                                                    25

(2) INFORMATION FOR SEQ ID NO:79:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:79:

GCAAAATGTA CTCAGCTTCA ATCAC                                  25

(2) INFORMATION FOR SEQ ID NO:80:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:80:

GTAAATGCAG TACTGTTCTG ATCC                                   24

(2) INFORMATION FOR SEQ ID NO:81:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:81:

GAATGCTTCA TTCTCATTGT TTAAGG                               26

(2) INFORMATION FOR SEQ ID NO:82:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:82:

GTCACTAGGA TTCCACAGAA CTTC                                   24

(2) INFORMATION FOR SEQ ID NO:83:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:83:

GAGGTAGGGC TTCCCTTCGC TA                                     22

(2) INFORMATION FOR SEQ ID NO:84:

(i) SEQUENCE CHARACTERISTICS:

(A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:84:

GCATAACAAG TGACAGGGTT AGTTA                                            25

(2) INFORMATION FOR SEQ ID NO:85:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:85:

GGTGCTCCTT CCTTACACTG GT                                               22

(2) INFORMATION FOR SEQ ID NO:86:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:86:

GACTACACAT AAACCCACCC CAG                                              23

(2) INFORMATION FOR SEQ ID NO:87:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:87:

GGGTACAGGA TTTCTAAGAA GTGG                                             24

(2) INFORMATION FOR SEQ ID NO:88:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:88:

GGAGAAAATT TCAGCTCATC TGAAG                                            25

(2) INFORMATION FOR SEQ ID NO:89:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i) MOLECULE TYPE: other nucleic acid, synthetic DNA (xi) SEQUENCE DESCRIPTION: SEQ ID NO:89:

GCTGAAGTTA AGCATTAATA CGCC                                         24

(2) INFORMATION FOR SEQ ID NO:90:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:90:

GCGGCTGTAA TGTGCAATGA TGT                                          23

(2) INFORMATION FOR SEQ ID NO:91:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:91:

GACAGCAACC TAATAACAGC TGTC                                         24

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:92:

GTCCTAGGCA CTTGTCACTA GG                                           22

(2) INFORMATION FOR SEQ ID NO:93:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:93:

GAGGGGACTT CCAAGAGTCT CT                                           22

(2) INFORMATION FOR SEQ ID NO:94:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:94:

GTCTTCAGGA AAATTGTAGT TACAG							25

(2) INFORMATION FOR SEQ ID NO:95:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:95:

GTTACAAACA CACACGAAGT TCCT							24

(2) INFORMATION FOR SEQ ID NO:96:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:96:

GACTTCCTAA GGCACACTCA GC							22

(2) INFORMATION FOR SEQ ID NO:97:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:97:

GTTTAACTAC CTCTCAGGTC ATGA							24

(2) INFORMATION FOR SEQ ID NO:98:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:98:

GTCGCCAAGG CTGTAGTGCA AT							22

(2) INFORMATION FOR SEQ ID NO:99:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:99:

GAAATAGGTA TCCCTTGATG TCGA							24

(2) INFORMATION FOR SEQ ID NO:100:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:100:

```
GACCAAGAAT TCAGTTCATC AGTT                                    24
```

(2) INFORMATION FOR SEQ ID NO:101:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:101:

```
GAATGAACCA GAGCCAGGAC AG                                      22
```

(2) INFORMATION FOR SEQ ID NO:102:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:102:

```
GCCTTGTATG TATGCCTGTG CC                                      22
```

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:103:

```
AAGAGTCCAC CAGGCCATGG A                                       21
```

(2) INFORMATION FOR SEQ ID NO:104:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:104:

```
TACCTTGTGT ACTTCTAGCT GAG                                     23
```

(2) INFORMATION FOR SEQ ID NO:105:

(i) SEQUENCE CHARACTERISTICS:
        (A) LENGTH: 17 base pairs

```
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:105:

GTTTTTTTTT TTTTTTA                                                17

(2) INFORMATION FOR SEQ ID NO:106:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:106:

GTTTTTTTTT TTTTTTG                                                17

(2) INFORMATION FOR SEQ ID NO:107:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:107:

GTTTTTTTTT TTTTTTC                                                17

(2) INFORMATION FOR SEQ ID NO:108:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:108:

CAGAGTGATG GATATCAA                                               18

(2) INFORMATION FOR SEQ ID NO:109:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:109:

ATGAAAGTGC CAGTGTGCCA TG                                          22

(2) INFORMATION FOR SEQ ID NO:110:

(i) SEQUENCE CHARACTERISTICS:
        (A) LENGTH: 22 base pairs
        (B) TYPE: nucleic acid
        (C) STRANDEDNESS: single
        (D) TOPOLOGY: linear
```

-continued (ii) MOLECULE TYPE: other nucleic acid, synthetic DNA (xi) SEQUENCE DESCRIPTION: SEQ ID NO:110:

CCCATCACCA TCTTCCAGGA GC                       22

(2) INFORMATION FOR SEQ ID NO:111:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:111:

TTCACCACCT TCTTGATGTC ATCATA                   26

IGA NEPHROPATHY-RELATED GENES

CROSS-REFERENCE TO RELATED APPLICATION

This is a continuation-in-part application of PCT/JP97/04468 filed on Dec. 5, 1997.

BACKGROUND OF THE INVENTION

1. Field of the Invention

The present invention relates to a novel DNA whose expression level fluctuates in leukocytes of IgA nephropathy patients in comparison with leukocytes of healthy persons, a process for isolating the DNA, a method for detecting the DNA, a novel protein encoded by the DNA an antibody recognizing the protein, a method for detecting the protein, and diagnosis and treatment of IgA nephropathy.

2. Brief Description of the Background Art

IgA nephropathy is a chronic glomerulonephritis which is characterized in that an IgA immune complex considered to be originated from blood deposits in glomerulus of the kidney. In Japan, the IgA nephropathy occupies 30% or more of primary renal diseases, having the highest frequency as a single renal disease, and 15 to 30% of the disease becomes renal insufficiency due to poor prognosis. However, since the cause of the disease of IgA nephropathy is still unclear, a fundamental therapeutic method has not been found. Additionally, definite diagnosis of IgA nephropathy imposes heavy burden on patients, because the method is carried out by taking out a portion of the kidney by biopsy and recognizing deposition of the IgA immune complex in mesangium by means of an immunological staining.

It has been reported that about 50% of the patients with IgA nephropathy have a high blood IgA level [*Diseases of the Kidney*, 5th edition (1993), *Nephron*, 29, 170 (1981)]. It is considered that B cells relate to the production of IgA in blood and T cells relate to the regulation of the production. Furthermore, it has been reported that the production of cytokine, such as interleukin 4, interleukin 5, interleukin 6 or TGF-β (transforming growth factors), is high in peripheral T cells of IgA nephropathy patients in comparison with healthy persons [*Clinical & Experimental Immunology*, 103, 125 (1996), *Kidney International*, 46, 862 (1994)] and that integrin, such as VLA (very late activation)-4 and VLA-5, are strongly activated in peripheral lymphocytes of IgA nephropathy patients [*Nephrology, Dialysis, Transplantation*, 10, 1342 (1995)]. On the basis of these facts, it is considered that, in IgA nephropathy, the production of IgA becomes excess due to abnormality in the immune system, the resulting IgA immune complex in blood deposits on the glomerulus, and activation of the complement system caused thereby and the like exert influence upon disorders of the glomerulus, but the cause of IgA nephropathy has not been reported.

Elucidation of the cause of IgA nephropathy and its treatment or diagnosis which can reduce a burden on patients are expected.

SUMMARY OF THE INVENTION

Accordingly, the present invention provides the development of a novel DNA related to IgA nephropathy, a method for obtaining the DNA, a novel protein related to IgA nephropathy, a method for producing the protein, an antibody recognizing the protein, and a therapeutic drug and a diagnostic drug using the above-described protein, DNA or antibody.

Specifically, the present invention relates to:

(1) a DNA related to IgA nephropathy, comprising a nucleotide sequence selected from the nucleotide sequences represented by SEQ ID NO:1 to NO:32 and SEQ ID NO:39 to NO:42, or a DNA which hybridizes with said DNA under stringent conditions;

(2) a DNA comprising a nucleotide sequence identical to continuous 5 to 60 residues in a nucleotide sequence selected from the nucleotide sequences represented by SEQ ID NO: 1 to NO:32 and SEQ ID NO:39 to NO:42, or a DNA comprising a sequence complementary to said DNA;

(3) a DNA comprising a nucleotide sequence selected from the nucleotide sequences represented by SEQ ID NO: 43 to NO:104;

(4) a method for detecting mRNA of an IgA nephropathy-related gene using the DNA according to any one of the above (1) to (3);

(5) an IgA nephropathy diagnostic agent comprising the DNA according to any one of the above (1) to (3);

(6) a method for inhibiting transcription of an IgA nephropathy-related gene or translation of mRNA of an IgA nephropathy-related gene using the DNA according to the above (2) or (3);

(7) an IgA nephropathy therapeutic agent comprising the DNA according to the above (2) or (3);

(8) a method for isolating a DNA related to IgA nephropathy from leukocytes of a patient with IgA nephropathy comprising conducting a differential display method;

(9) a protein comprising an amino acid sequence selected from the amino acid sequences represented by SEQ ID NO:33 to NO:38; or a protein comprising an amino acid sequence in which one or several amino acids are deleted, substituted or added in the amino acid sequence of said protein, and having an activity related to IgA nephropathy;

(10) a DNA encoding the protein according to the above (9);

(11) a recombinant DNA obtained by inserting the DNA according to the above (10) into a vector;

(12) a transformant obtained by introducing the recombinant DNA according to the above (11) into a host cell;

(13) a method for producing the protein according to the above (9), comprising: culturing the transformant according to the above (12) in a medium to produce and accumulate said protein in the culture; and recovering said protein from the resulting culture;

(14) an antibody which recognizes the protein according to the above (9);

(15) a method for immunologically detecting the protein according to the above (9) using the antibody according to the above (14);

(16) an IgA nephropathy diagnostic agent comprising the antibody according to the above (14);

(17) an IgA nephropathy therapeutic agent comprising the antibody according to the above (14);

(18) a composition comprising the DNA according to any one of the above (1) to (3) and a diagnostic acceptable carrier;

(19) a composition comprising the DNA according to the above (2) or (3) and a pharmaceutical acceptable carrier;

(20) a composition comprising the antibody according to the above (14) and a diagnostic acceptable carrier; and

(21) a composition comprising the antibody according to the above (14) and a pharmaceutical acceptable carrier.

DETAILED DESCRIPTION OF THE INVENTION

This application is based on Japanese application No. 8-325763 filed on Dec. 5, 1996 and PCT/JP97/04468 filed on Dec. 5, 1997, the entire contents of which are incorporated hereinto by reference.

The DNA of the present invention is a DNA related to IgA nephropathy (referred to as "IgA nephropathy-related DNA" hereinafter). Examples include a DNA comprising a nucleotide sequence selected from the nucleotide sequences represented by SEQ ID NO:1 to NO:1 to NO:32 and SEQ ID NO:39 to NO:42, and a DNA which hybridizes with the DNA under stringent conditions.

The DNA which hybridizes under stringent conditions with a DNA comprising a nucleotide sequence selected from the nucleotide sequences represented by SEQ ID NO:1 to NO:32 and SEQ ID NO:39 to NO:42 means a DNA which is obtained by colony hybridization, plaque hybridization, Southern blot hybridization or the like using, as a probe, a DNA comprising a nucleotide sequence selected from the nucleotide sequences represented by SEQ ID NO:1 to NO:32 and SEQ ID NO:39 to NO:42. Examples include DNA which can be identified by carrying out hybridization at 65° C. in the presence of 0.7–1.0M NaCl using a filter on which a MM prepared from colonies or plaques is immobilized, and then washing the filter with 0.1× to 2×SSC solution (the composition of 1×SSC comprises 150 mM sodium chloride and 15 mM sodium citrate) at 65° C.

The hybridization can be carried out in accordance with known methods described in, for example, *Molecular Cloning, A Laboratory Manual*, Second Edition, Cold Spring Harbor Laboratory Press (1989) (referred to as "*Molecular Cloning*, 2nd ed." hereinafter), *Current Protocols in Molecular Biology*, John Wiley & Sons (1987–1997) (referred to as "*Current Protocols in Molecular Biology*" hereinafter), *DNA Cloning 1: Core Techniques, A Practical Approach*, Second Edition, Oxford University (1995) or the like. Specific examples of the DNA which can be hybridized include a DNA having a homology of 60% or more with a nucleotide sequence selected from the nucleotide sequences represented by SEQ ID NO:1 to NO:32 and SEQ ID NO:39 to NO:42, preferably a DNA having a homology of 80% or more, and more preferably a DNA having a homology of 95% or more.

Also, the DNA of the present invention includes an oligonucleotide and antisense oligonucleotide containing a partial sequence of the IgA nephropathy-related DNA.

Examples of the oligonucleotide include oligonucleotides comprising a sequence identical to a sequence of continuous 5 to 60 residues, preferably continuous 10 to 50 residues, in a nucleotide sequence selected from the nucleotide sequences represented by SEQ ID NO:1 to NO:32 and SEQ ID NO:39 to NO:42. Examples of the antisense oligonucleotide include antisense oligonucleotides of the oligonucleotides. Specific examples include oligonucleotides comprising a nucleotide sequence selected from the nucleotide sequences represented by SEQ ID NO:43 to NO:104.

Examples of the protein of the present invention include proteins having an activity related to IgA nephropathy. Specific examples include a protein comprising an amino acid sequence selected from the amino acid sequences represented by SEQ ID NO:33 to NO:38, and a protein comprising an amino acid sequence in which one or several amino acids are deleted, substituted or added in the amino acid sequence of said protein and having an activity related to IgA nephropathy.

The protein comprising an amino acid sequence in which one or several amino acids are deleted, substituted or added in the amino acid sequence of the protein that has an amino acid sequence selected from the amino acid sequences represented by SEQ ID NO:33 to NO: 38 and having an activity related to IgA nephropathy can be prepared in accordance with known methods described in, for example, *Molecular Cloning*, 2nd ed., *Current Protocols in Molecular Biology*, *Nucleic Acids Research*, 10, 6487 (1992), *Proc. Natl. Acad. Sci. USA*, 79, 6409 (1982), *Gene*, 34, 315 (1985), *Nucleic Acids Research*, 13, 4431 (1925), *Proc. Natl. Acad. Sci. USA*, 82, 488 (1985) and the like.

Examples of the antibody of the present invention include antibodies which recognize the above-described proteins.

The present invention is described in detail.

1. Preparation of IgA Nephropathy-related DNA

Taking note of the difference in the expression quantity of mRNA in leukocytes between patients with IgA nephropathy and healthy persons, the IgA nephropathy-related DNA is isolated using the differential display method [*FEBS Letters*, 351, 231 (1994)]. That is, an amplified cDNA fragment of a novel gene (referred to as "IgA nephropathy-related gene" hereinafter) whose expression level increases or decreases significantly in leukocytes of a patient with IgA nephropathy as compared with leukocytes of a healthy person is obtained by subjecting total RNA or mRNA extracted from cells to the polymerase chain reaction (PCR) using various primers.

This method is described brow.

Total RNA or mRNA is prepared from leukocytes of patients with IgA nephropathy and leukocytes of healthy persons.

Examples of the method for the preparation of total RNA include guanidine thiocyanate-cesium trifluoroacetate method [*Methods in Enzymol.*, 154, 3 (1987)] and the like.

Examples of the method for preparing poly(A)$^+$ RNA from total RNA include oligo(dT)-immobilized cellulose column method (*Molecular Cloning*, 2nd ed.) and the like.

The mRNA can be also prepared using a kit, such as Fast Track mRNA Isolation Kit (manufactured by Invitrogen), Quick Prep mRNA Purification Kit (manufactured by Pharmacia) or the like.

Using an anchor primer, cDNA is synthesized in the usual way from the RNA extracted by the above-described method from leukocytes of a patient with IgA nephropathy or leukocytes of a healthy person, and then the cDNA is amplified by subjecting it to PCR using an anchor primer having a 5'-end labeled with fluorescence and an arbitrary primer.

The anchor primer is a primer in which an oligonucleotide of adenine, guanine or cytosine, excluding thymidine, is added to the 3'-end of an oligo(dT) sequence which hybridizes with a 3'-end poly(A) sequence of mRNA, and the primer can be synthesized using DNA Synthesizer Model 392 (manufactured by Perkin-Elmer) or the like.

The arbitrary primer is an oligonucleotide which amplifies various cDNA sequences and can yield a large number of amplified DNA fragments by a single reaction. Examples include OPD-1 to 20, OPE-1 to 20, OPV-1 to 20 (manufactured by Operon Technologies), and the like. Preferably, the arbitrary primer may have a length of about 10 bases.

Each of the DNA amplified by PCR is subjected to polyacrylamide gel electrophoresis, and the amount of fluorescence of the resulting bands is measured using Fluoro Imager (manufactured by Molecular Dynamics).

By comparing intensities of fluorescence of respective bands, a portion of the gel, which corresponds to the position of band where the intensities of fluorescence are fluctuated between the IgA nephropathy patient and healthy person, is cut off and the DNA fragment contained in the gel is amplified by PCR.

The nucleotide sequence of the DNA is determined by inserting the amplified DNA fragment into a vector, directly or after blunt-ending its termini using a DNA polymerase, in the usual way and then analyzing it by a usually used nucleotide sequence analyzing method such as the dideoxy method of Sanger et al. [*Proc. Natl. Acad. Sci. USA*, 74, 5463 (1977)] or using a nucleotide sequence analyzer such as 373A DNA Sequencer (manufactured by Perkin Elmer).

Examples of the vector used for the integration of the amplified DNA fragment include pBluescript KS(+) (manufactured by Stratagene), pDIRECT [*Nucleic Acids Research*, 18, 6069 (1990)], pPCR-Script Amp [manufactured by Stratagene, *Strategies*, 5, 6264 (1992)], pT7Blue (manufactured by Novagen), pCR II [manufactured by Invitrogen, *Biotechnology*, 9, 657 (1991)], pCR-TRAP (manufactured by Genehunter), pNoTA$_{T7}$ (manufactured by 5'→3') and the like.

Novelty of the nucleotide sequence determined in this manner can be verified by searching a data base, such as GenBank, EMBL, DDBJ and the like, using a homology searching program, such as blast and the like, thereby finding that there is no nucleotide sequence which shows an obvious homology that coincides with the nucleotide sequences in the data base.

Examples of the thus obtained partial DNA fragment of cDNA of the IgA nephropathy-related gene include DNA comprising a nucleotide sequence selected from the nucleotide sequences represented by SEQ ID NO:7 to NO:32 and SEQ ID NO:39 to NO:42.

When the DNA obtained by the re-described method is a partial DNA fragment of cDNA which corresponds to IgA nephropathy-related mRNA, full-length cDNA can be obtained by the following method (1) or (2) using the DNA obtained by the above-described method.

(1) Application of cDNA Library

A full-length cDNA can be obtained by carrying out screening according to hybridization using the above-described DNA fragment as the probe and various cDNA libraries.

The method for the preparation of cDNA libraries is described below.

Examples of the method for the preparation of cDNA libraries include methods described in *Molecular Cloning*, 2nd. ed., *Current Protocols in Molecular Biology*, or *DNA Cloning 1: Core Techniques, A Practical Approach*, Second Addition, Oxford University Press (1995), or methods using a commercially available kit, such as SUPERSCRIPT Plasmid System for cDNA Synthesis and Plasmid Cloning (manufactured by Life Technologies) or ZAP-cDNA Synthesis Kit (manufactured by Stratagene). Additionally, commercially available cDNA libraries, such as a human leukocyte cDNA library (manufactured by Life Technologies) and the like, can be also used.

In preparing the cDNA library, any one of phage vectors, plasmid vectors and the like can be used as the cloning vector which replicates autonomously in *Escherichia coli* K12. Examples include ZAP Express (manufactured by Stratagene, *Strategies*, 5, 58 (1992)), pBluescript II SK(+) [*Nucleic Acids Research*, 17, 9494 (1989)], λZAP II (manufactured by Stratagene), λgt10, λgt11[*DNA Cloning, A Practical Approach*, 1, 49 (1985)], λExCell (manufactured by Pharmacia), pcD2[*Mol. Cell. Biol.*, 3, 280 (1983)], pUC18 [*Gene*, 33, 103 (1985)], and the like.

With regard to the *Escherichia coli* used to transform with the vector containing the cDNA, any microorganism belonging to *Escherichia coli* can be used. Examples include *Escherichia coli* XL1-Blue MRF' [manufactured by Stratagene, *Strategies*, 5, 81 (1992)], *Escherichia coli* C600 [*Genetics*, 39, 440 (1954)], *Escherichia coli* Y1088[*Science*, 222, 778 (1983)], *Escherichia coli* Y1090[*Science*, 222, 778 (1983)], *Escherichia coli* NM522[*J. Mol. Biol.*, 166, 1 (1983)], *Escherichia coli* K802[*J. Mol. Biol.*, 16, 118 (1966)], *Escherichia coli* JM105[*Gene*, 3, 275 (1985)], and the like.

A cDNA clone can be selected from the cDNA library according to a colony hybridization or plaque hybridization method (*Molecular Cloning*, 2nd ed.) using a probe labeled with an isotope or digoxigenin.

The DNA of interest can be obtained from the thus selected clone in the usual way.

(2) The DNA of interest can be also obtained by the 5'-RACE (rapid amplification of cDNA ends) and 3'-RACE method [*Proc. Natl. Acad. Sci. USA*, 85, 8998 (1988)] in which cDNA is synthesized from mRNA by the above-described method, adapters are added to both ends of the cDNA and then PCR is carried out using primers based on the nucleotide sequence of the adapter and the nucleotide sequence of the amplified fragment.

Nucleotide sequence of the DNA obtained by these methods can be determined by the above-described nucleotide sequence determining method. Novelty of the sequence can be also verified by the above-described method.

Examples of the full-length cDNA of the IgA nephropathy-related gene obtained in this manner include DNAs having the nucleotide sequences represented by SEQ ID NO:1 to NO:6.

Once a DNA of IgA nephropathy-related gene is obtained and a nucleotide sequence thereof is determined in the above-described manner, the DNA of interest can be obtained by PCR [*PCR Protocols*, Academic Press (1990)] by preparing primers based on the nucleotide sequence and using cDNA synthesized from the mRNA or a cDNA library as the template. Alternatively, the DNA of interest may be prepared by chemical synthesis using a DNA synthesizer based on the determined DNA nucleotide sequence. Examples of the DNA synthesizer include DNA Synthesizer Model 392 (manufactured by Perkin-Elmer) using the phosphoramidite method.

On the basis of the nucleotide sequence information of the above-described DNA and DNA fragments, an oligonucleotide having a partial sequence of the IgA nephropathy-related DNA and a corresponding antisense oligonucleotide can be prepared.

Examples of the oligonucleotide or antisense oligonucleotide include a sense primer corresponding to a 5'-end side nucleotide sequence, and an antisense primer corresponding to a 3'-end side nucleotide sequence, of a portion of the mRNA to be detected. In this case, the base corresponding to uracil in mRNA corresponds to thymidine in the oligonucleotide primer.

As the sense primer and antisense primer, it is preferred to use oligonucleotides in which melting point ($T_m$) and the number of bases are not significantly different from each other, and those which have 5 to 60 bases, preferably 10 to 50 bases, can be used.

Also, an analogue of the oligonucleotide can be used in the present invention. For example, the methyl or phosphorothioate analogue of the oligonucleotide may be used.

Examples of the oligonucleotide or antisense oligonucleotide comprising a partial sequence of the IgA nephropathy-related DNA include an oligonucleotide comprising a nucleotide sequence selected from the nucleotide sequences represented by SEQ ID NO:43 to NO:104.

2. Production of Protein Having an Activity Related to IgA Nephropathy

The full-length cDNA of IgA nephropathy-related gene obtained by the method described in the above section 1 encodes a protein having an activity related to IgA nephropathy (referred to as "IgA nephropathy-related protein" hereinafter). The IgA nephropathy-related protein is prepared by expressing the IgA nephropathy-related gene in a host cell as shown below. A DNA fragment having a suitable length containing a portion encoding the protein is prepared from the full-length cDNA as occasion demands. An expression plasmid of the protein is prepared by inserting the DNA fragment or the full-length cDNA into a downstream site of the promoter in the expression vector. The expression plasmid is introduced into a host cell suitable for the expression vector.

As the host cell, any cell can be used so long as it can express the gene of interest. Examples include bacteria belonging to the genus *Escherichia, Serratia, Corynebacterium, Brevibacterium, Pseudomonas, Bacillus, Microbacterium* and the like, yeasts belonging to the genus *Kluyveromyces, Saccharomyces, Schizosaccharomyces, Trichosporon, Schwanniomyces* and the like, animal cells, insect cells, and the like.

Examples of the expression vector include those which can replicate autonomously in the just described host cell or can be integrated into chromosome and have a promoter at such a position that the IgA nephropathy-related gene can be transcribed.

When a bacterium or the like is used as the host cell, it is preferred that the IgA nephropathy-related gene expression vector can replicate autonomously in the bacterium and is a recombinant vector constructed with a promoter, a ribosome binding sequence, the IgA nephropathy-related gene and a transcription termination sequence. A promoter controlling gene may also be contained.

Examples of the expression vector include pBTrp2, pBTac1 and pBTac2 (all available from Boehringer Mannheim Co.), pKK233-2 (manufactured by Pharmacia), pSE280 (manufactured by Invitrogen), pGEMEX-1 (manufactured by Promega), pQE-8 (manufactured by QIAGEN), pKYP10 (Japanese Published Unexamined Patent Application No 110600/83), pKYP200 [*Agric. Biol. Chem.*, 48, 669 (1984)], pLSA1[*Agric. Biol. Chem.*, 53, 277 (1989)], pGEL1[*Proc. Natl. Acad. Sci. USA*, 82, 4306 (1985)], pBluescript II SK(-) (manufactured by Stratagene), pGEX (manufactured by Pharmacia), pET-3 (manufacture by Novagen), pTerm2 (U.S. Pat. Nos. 4,686,191, 4,939,094 and 5,160,735), pUB110, pTP5, pC194, pEG400[*J. Bacteriol.*, 172, 2392 (1990)] and the like.

With regard to the promoter, any promoter can be used so long as it can drive the expression in the host cell. Examples include promoters originated from *Escherichia coli*, phage and the like (for example, trp promoter (Ptrp), lac promoter (Plac), $P_L$ promoter, $P_R$ promoter, T7 promoter and the like), SPO1 promoter, SPO2 promoter, penP promoter and the like. Also, artificially designed and modified promoters, such as a promoter in which two Ptrp are linked in series (Ptrp×2), tac promoter, letI promoter [*Gene*, 44, 29 (1986)] and lacT7 promoter and the like, can be used.

With regard to the ribosome binding sequence, any sequence can be used so long as it can effect the expression in the host cell. However, it is preferred to use a plasmid in which the space between Shine-Dalgarno sequence and the initiation codon is adjusted to an appropriate distance (for example, 6 to 18 bases).

Production efficiency of the protein of interest can be improved by substituting a base in a nucleotide sequence which encodes the IgA nephropathy protein of the present invention so as to form a codon suitable for the expression of a host.

The transcription termination sequence is not always necessary for the expression of the IgA nephropathy-related gene of the present invention. However, it is preferred to arrange the transcription terminating sequence at just downstream of the structural gene.

Examples of the host cell include microorganisms belonging to the genus *Escherichia, Serratia, Bacillus, Brevibacterium, Corynebacterium, Microbacterium, Pseudomonas,* and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Seratia ficaria, Seratia fonticola, Seratia liquefaciens, Seratia marcescens, Bacillus subtilis, Bacillus amyloliquefaciens, Brevibacterium ammoniagenes, Brevibacterium immariophilum* ATCC 14068, *Brevibacterium saccharolyticum* ATCC 14066, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110 and the like.

With regard to the method for the introduction of the recombinant vector, any one of the known methods for introducing DNA into the just described host calls, such as a method in which calcium ion is used [*Proc. Natl. Acad. Sci. USA*, 69, 2110 (1972)], a protoplast method (Japanese Published Unexamined Patent Application No. 2483942/88), the methods described in *Gene*, 17, 107 (1982) and *Molecular & General Genetics*, 16, 111 (1979) and the like, can be used.

When yeast is used as the host cell, YEp13 (ATCC 37115), YEp24 (ATCC 37051), YCp50 (ATCC 37419), pHS19, pHS15 or the like is used as the expression vector.

Any promoter can be used so long as it can drive the expression in yeast. Examples include PHO5 promoter, PGK promoter, GAP promoter, ADH promoter, gal 1 promoter, gal 10 promoter, heat shock protein promoter, MF α1 promoter, CUP 1 promoter and the like.

Examples of the host cell include *Saccharomyces cerevisiae, Schizosaccharomyces pombe, Kluyveromyces lactis, Trichosporon pullulans, Schwanniomyces alluvius* and the like.

With regard to the method for the introduction of the recombinant vector, any one of known methods for introducing DNA into yeast, such as an electroporation method [*Methods. Enzymol.*, 194, 182 (1990)], a spheroplast method [*Proc. Natl. Acad. Sci. USA*, 75, 1929 (1978)], a lithium acetate method [*J. Bacteriol.*, 153, 163 (1983)], a method described in *Proc. Natl. Acad. Sci. USA*, 75, 1929 (1978) and the like, can be used.

When animal cells are used as the host calls, pcDNAI and pcDM8 (both available from Funakoshi), pAGE107 [Japanese Published Unexamined Patent Application No. 22979/91; *Cytotechnology*, 3, 133 (1990)], pAS3—3 (Japanese Published Unexamined Patent Application No.

227075/90), pcDM8[*Nature*, 329, 840 (1987)], pcDNAI/Amp (manufactured by Invitrogen), pREP4 (manufactured by Invitrogen), pAGE103[*J. Biochem.*, 101, 1307 (1987)], pAGE210 and the like can be exemplified as the expression vector.

Any promoter can be used so long as it can drive the expression in animal cell. Examples include a promoter of IE (immediate early) gene of cytomagalovirus (CMV), an early promoter of SV40, a promoter of retrovirus, a metallothionein promoter, a heat shock promoter, an SRα promoter and the like. Also, the enhancer of the IE gene of human CMV may be used together with the promoter.

Examples of the host call include human Namalwa cell, monkey COS cell, Chinese hamster CHO cell, HST5637 (Japanese Published Unexamined Patent Application No. 299/88), and the like.

With regard to the method for the introduction of the recombinant vector into animal cells, any one of the known methods for introducing DNA into animal cells, such as an electroporation method [*Cytotechnology*, 3, 133 (1990)], a calcium phosphate method (Japanese Published Unexamined Patent Application No. 227075/90), a lipofection method [*Proc. Natl. Acad. Sci. USA*, 84, 7413 (1987)] and the method described in *Virology*, 52, 456 (1973), can be used. Preparation and culturing of transformants can be carried out in accordance with the method described in Japanese Published Unowned Patent Application No. 227075/90 or Japanese Published Unexamined Patent Application No. 257891/90.

When an insect cell is used as the host cell, the protein can be expressed by known methods described in, for example, *Bacurovirus Expression Vectors, A Laboratory Manual, Current Protocols in Molecular Biology*, supplement 1–38 (1987–1997) *Bio/Technology*, 6, 47 (1988), or the like.

That is, a recombinant gene transfer vector and bacurovirus are simultaneously inserted into an insect cell to obtain a recombinant virus in an insect cell culture supernatant, and then the insect cells are infected with the thus obtained recombinant virus to effect expression of the protein.

Examples of the gene introducing vector used in the method include pVL1392, pVL1393, pBlueBacIII (all manufactured by Invitrogen), and the like.

Examples of the bacurovirus include *Autographa californica* nuclear polyhedrosis virus with which insects of the family Barathra are infected, and the like.

Examples of the insect cell include *Spodoptera frugiperda* oocytes Sf9 and Sf21 (*Bacurovirus Expression Vectors, A Laboratory Manual*, W. H. Freeman and Company, New York, (1992)), *Trichoplusia ni* oocyte High 5 (manufactured by Invitrogen) and the like.

The method for the co-transfer of the above-described recombinant gene transfer vector and the above-described bacurovirus for the preparation of the recombinant virus include calcium phosphate method (Japanese Published Unexamined Patent Application No. 227075/90), lipofection method [*Proc. Natl. Acad. Sci. USA*, 84, 7413 (1987)] and the like.

With regard to the gene expression method, a secretion production, a fusion protein expression and the like can be effected in accordance with the method described in *Molecular Cloning*, 2nd ed., in addition to the direct expression.

When expressed in a yeast, an animal cell or a insect cell, a glycosylated protein can be obtained.

The IgA nephropathy-related protein can be produced by culturing a transformant comprising a recombinant DNA containing the IgA nephropathy-related gene in a culture medium to produce and accumulate the IgA nephropathy-related protein, and recovering the protein from the resulting culture.

Culturing of the transformant used in the production of the IgA nephropathy-related protein of the present invention in a culture medium is carried out in accordance with a usual method used in culturing of respective host cells.

When the transformant of the present invention is an prokaryote, such as *Escherichia coli* or the like, or an eukaryote, such as yeast or the like, the medium used in culturing of these microorganisms may be either a natural medium or a synthetic medium, so long as it contains a carbon source, a nitrogen source, an inorganic salt and the like which can be assimilated by the microorganisms and can perform culturing of the transformant efficiently.

Examples of the carbon source include those which can be assimilated by respective microorganisms, such as carbohydrates (for example, glucose, fructose, sucrose, molasses containing them, starch, starch hydrolysate, and the like), organic acids (for example, acetic acid, propionic acid, and the like), and alcohols (for example, ethanol, propanol, and the like).

Examples of the nitrogen source include ammonia, various ammonium salts of inorganic acids or organic acids (for example, ammonium chloride, ammonium sulfate, ammonium acetate, ammonium phosphate, and the like), other nitrogen-containing compounds, peptone, meat extract, yeast extract, corn steep liquor, casein hydrolysate, soybean meal and soybean meal hydrolysate, various fermented cells and hydrolysates thereof, and the like.

Examples of inorganic substance used in the culture medium include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

The culturing is carried out under aerobic conditions by shaking culture, aeration stirring culture or the like means. The culturing temperature is preferably from 15 to 45° C., and the culturing time is generally from 16 hours to seven days. The pH of the medium is maintained at 3.0 to 9.0 during the culturing. Adjustment of the medium pH is carried out using an inorganic or organic acid, an alkali solution, urea, calcium carbonate, ammonia and the like.

Also, antibiotics (for example, ampicillin, tetracycline, and the like) may be added to the medium during the culturing as occasion demands.

When a microorganism transformed with an expression vector containing an inducible promoter is culture, an inducer may be added to the medium as occasion demands. For example, isopropyl-β-D-thiogalactopyranoside (IPTG) or the like may be added to the medium when a microorganism transformed with an expression vector containing lac promoter is cultured, or indoleacrylic acid (IAA) or the like may by added thereto when a microorganism transformed with an expression vector containing trp promoter is cultured.

Examples of the medium used in the culturing of a transformant obtained using an animal cell as the host call include RPMI 1640 medium [*The Journal of the American Medical Association*, 199, 519 (1967)], Eagle's MEM medium [*Science*, 122, 501 (1952)], Dulbecco's modified MEM medium [*Virology*, 8, 396 (1959)], 199 Medium [*Proceeding of the Society for the Biological Medicine*, 73, 1 (1950)], and any one of these media further supplemented with fetal calf serum.

The culturing is carried out generally at pH of 6 to 8 and at a temperature of 30 to 40° C. for a period of 1 to 7 days in the presence of 5% $CO_2$.

As occasion demands, antibiotics (for example, kanamycin, penicillin, and the like) may be added to the medium during the culturing.

Examples of the medium used in the culturing of a transformant obtained using an insect cell as the host cell, include TNM-FH medium (manufactured by Pharmingen), Sf-900 II SFM (manufactured by Life Technologies), ExCell 400 or ExCell 405 (both manufactured by JRH Biosciences), Grace's Insect Medium [Grace T. C. C., *Nature*, 195, 788 (1962)], and the like.

The culturing is carried out generally at pH of 6 to 7 and at a temperature of 25 to 30° C. for a period of 1 to 5 days.

Additionally, antibiotics (for example, gentamicin, and the like) may be added to the medium during the culturing as occasion demands.

When the protein of the present invention having an activity related to IgA nephropathy is isolated and purified from a culture of the transformant of the present invention, usual methods for the isolation and purification of enzymes may be used.

For example, when the protein of the present invention is expressed in a dissolved state inside the cells, the cells after completion of the culturing are recovered by centrifugation, suspended in a buffer of aqueous system and then disrupted using ultrasonic oscillator, French press, Manton Gaulin homogenizer, dynomill or the like to obtain a cell-free extract. A purified product can be obtained from a supernatant fluid prepared by centrifugation of the cell-free extract, by employing a technique or a combination of techniques, such as solvent extraction, salting out with ammonium sulfate or the like, desalting, precipitation with organic solvents, anion exchange chromatography using a resin (for example, diethylaminoethyl (DEAE)-Sepharose, DIAION HPA-75 (manufactured by Mitsubishi Chemical), or the like), cation exchange chromatography using a resin (for example, S-Sepharose FF (manufactured by Pharmacia), or the like), hydrophobic chromatography using a resin (for example, butyl-Sepharose, phenyl-Sepharose, or the like), gel filtration using a molecular sieve, affinity chromatography, chromatofocusing, electrophoresis (for example, isoelectric focusing).

Also, when the protein is expressed inside the cells in the form of an inclusion body, the cells are recovered, disrupted and centrifuged, thereby recovering the inclusion body of the protein as a precipitated fraction. The recovered inclusion body of the protein is solubilized using a protein denaturing agent. The protein is renatured into a normal solid structure by diluting or dialyzing the thus-obtained solubilized solution to lower the protein denaturing agent in the solubilized solution, and then a purified product of the protein is obtained by the isolation purification method in the same manner as described above.

When the protein of the present invention or a derivative thereof, such as a sugar-modified product, is secreted outside the cells, the protein or the derivative can be recovered from the culture supernatant. That is, the purified product can be obtained by recovering culture supernatant from the culture by a technique, such as centrifugation or the like, and then subjecting the culture supernatant to the above-described isolation purification method.

Examples of the protein obtained in this manner include proteins having an amino acid sequence selected from the amino acid sequences represented by SEQ ID NO:33 to NO:38.

Additionally, the protein expressed by the above-described method can be produced by a chemical synthesis method, such as Fmoc method (fluoronylmethyloxycarbonyl method), tBoc method (t-butyloxycarbonyl method) or the like. It can be also synthesized using a peptide synthesizer available from Sowa Boeki (manufactured by Advanced chenTech, USA), Perkin-Elmer Japan (manufactured by Perkin-Elmer, USA), Pharmacia Biotech (manufactured by Pharmacia Biotech, Sweden), Aroka (manufactured by Protein Technology Instrument, USA), KURABO (manufactured by Synthecell-Vega, USA), Japan PerSeptive Limited (manufactured by PerSeptive, USA) or Shimadzu Corporation.

3. Preparation of Antibody Which Recognizes the Protein of the Present Invention A purified product of the whole length or a partial fragment of the protein obtained by the method described in the above section 2 or a peptide having a partial amino acid sequence of the protein of the present invention is used as the antigen. The antigen is administered to animal by intravenous or intraperitoneal injection together with an appropriate adjuvant (for example, complete Freund's adjuvant, aluminum hydroxide gel, pertussis vaccine, or the like).

Examples of the animals used include rabbits, goats, 3- to 20-weak-old rats, mice, hamsters and the like.

Preferable dosage of antigen is 50 to 100 $\mu$g per animal.

When a peptide is used as the antigen, it is preferred to use the peptide as the antigen after binding it covalently to a carrier protein, such as keyhole limpet haemocyanin, bovine thyroglobulin or the like. The peptide used as the antigen can be synthesized using a peptide synthesizer.

Administration of the antigen is carried out 3 to 10 times at one- to two-week intervals after the first administration. A blood sample is recovered from the fundus of the eye 3 to 7 days after each administration, and the serum is tested, for example, by enzyme immunoassay (Enzyme-linked Immmosorbent Assay (ELISA), published by Igaku Shoin (1976); *Antibodies—A Laboratory Manual*, Cold Spring Harbor Laboratory (1988)) as to whether it is reactive with the antigen used for immunization. A non-human mammal whose serums shows a sufficient antibody titer against the antigen used for immunization is submitted for use as the supply source of serum or antibody producing cells.

A polyclonal antibody can be prepared by isolating and purifying it from the serum.

A monoclonal antibody can be prepared by preparing a hybridoma through fusion of the antibody producing cells with myeloma cells of a non-human mammal and culturing the hybrid a, or administering the hybridoma to an animal to induce ascites tumor in the animal, and then isolating and purifying it from the culture medium or ascitic fluid.

Examples of the antibody producing cells include spleen cells, lymph nodes and antibody producing cells in peripheral blood. Particularly, spleen cells are preferred.

Examples of the myeloma cells include cell lines derived from mouse, such as P3-X63Ag8-U1 (P3-U1) cell line [*Current Topics in Microbiology and Immunology*, 18, 1–7 (1978)], P3-NS1/1-Ag41 (NS-1) cell line [*European J. Immunology*, 6, 511–519 (1976)], SP2/O-Ag14 (SP-2) cell line [*Nature*, 256, 269–270 (1978)], P3-X63-Ag8653 (653) cell line [*J. Immunology*, 123, 1548–1550 (1979)], P3-X63-Ag8 (X63) cell line [*Nature*, 5, 495–497 (1975)] and the like, which are 8-azaguanine-resistant mouse (BALB/c) myeloma call lines.

Hybridoma calls can be prepared in the following manner. Antibody producing cells and myeloma cells are fused, suspended in HAT medium (normal medium supplemented with hypoxanthine, thymidine and aminopterin) and then cultured for 7 to 14 days. After the culturing, a portion of the culture supernatant is sampled and tested, for example, by enzyme immunoassay to select those which can react with the antigen but not with protein which does not contain the antigen. Thereafter, cloning is carried out by limiting dilution analysis, and a hybridoma which shows stable and high antibody titer by enzyme immunoassay is selected as monoclonal antibody producing hybridoma cells.

With regard to the method for the isolation and purification of the polyclonal antibody or monoclonal antibody, centrifugation, ammonium sulfate precipitation, caprylic acid precipitation, or chromatography using a DEAE-Sepharose column, an anion exchange column, a protein A or G column, a gel filtration column and the like may be employed alone or as a combination thereof.

4. Application of IgA Nephropathy-related DNA, Protein or Antibody (1) Using the DNA described in the above section 1, mRNA of the IgA nephropathy-related gene of the present invention can be detected by northern hybridization (*Molecular Cloning*, 2nd ed.), PCR [*PCR Protocols*, Academic Press (1990)], RT (reverse-transcribed)-PCR and the like. Particularly, RT-PCR is simple and easy and can therefore be applied to the diagnosis of IgA nephropathy.

For example, diagnosis of IgA nephropathy may be effected by carrying out PCR using the DNA described in the above section 1 which corresponds to the mRNA to be detected as a pair of oligonucleotide primers and detecting the amplified fragment. In that case, the nucleotide sequence moiety to be amplified may be any nucleotide sequence region of the mRNA, but a nucleotide sequence region which has a length of from 50 bp to 2 kbp and does not contain a sequence rich in a repeating sequence or GC (guanine-cytosine) bases is preferred.

(2) Using the antisense oligonucleotide (RNA/DNA) described in the above section 1[*Chemistry*, 46, 681 (1991), *Biotechnology*, 9, 358 (1992)], treatment of IgA nephropathy can be effected by inhibiting transcription of DNA or translation of mRNA.

An example of the antisense oligonucleotide (RNA/DNA) of the above section 1 used in this case is an antisense oligonucleotide which has a partial nucleotide sequence, preferably a sequence of from 10 to 50 bases in the translation initiation region, of a DNA which encodes the protein described in the above section 2.

(3) Using the DNA described in the above section 1, the IgA nephropathy-related protein of the present invention can be obtained by the method described in the above section 2.

(4) Using the protein described in the above section 2 as the antigen, antibodies can be produced by the method described in the above section 3.

(5) Using the ant described in the above section 3, the IgA nephropathy-related protein can be detected or determined immunologically.

Examples of the immunological detection method include ELISA method using a microtiter plate, fluorescent antibody technique, western blot technique, immunohistochemical staining and the like.

Examples of the immunological determination method include sandwich ELISA method in which, among antibodies which react with the protein of the present invention in solution, two monoclonal antibodies having different epitopes are used and radioimmunoassay method in which the protein of the present invention labeled with radioactive isotope, such as $^{125}$I or the like, and an antibody which recognizes the protein of the present invention are used.

(6) Using the antibody described in the above section 3, the presence or absence of IgA nephropathy in a person to be inspected can be diagnosed by immunologically detecting or determining an IgA nephropathy-related protein in leukocytes collected from a healthy person and the person to be inspected, comparing its amounts in the healthy person and person to be inspected and then examining the quantitative fluctuation. As a specific sample to be tested, leukocytes separated from peripheral blood samples of a healthy person and a person to be inspected can be used. Additionally, when the IgA nephropathy-related protein to be detected is a protein secreted from leukocytes, the presence or absence of IgA nephropathy in a person to be inspected can be detected and diagnosed by immunologically detecting or determining the protein in blood plasma samples collected from a healthy person and the person to be inspected, comparing its amounts in the healthy person and person to be inspected and then examining its quantitative fluctuation.

(7) The antibody described in the above section 3 can be applied to the treatment or prevention of IgA nephropathy.

When the DNA, protein and antibody is used for the diagnosis, treatment or prevention of IgA nephropathy, a diagnostically or pharmacologically acceptable carrier may be added.

EXAMPLES

Examples of the present invention are given below by way of illustration and not by way of limitation.

Example 1

Differential Display of Leukocytes of IgA Nephropathy Patients and Healthy Persons (1) Preparation of total RNA from leukocytes of IgA nephropathy patients and healthy persons A 20 ml portion of blood was collected from each of five IgA nephropathy patients and five healthy persons.

This was mixed with 500 μl of 1,000 units/ml heparin solution to inhibit coagulation, transferred into a centrifugation tube and then centrifuged at 3,300 rpm for 15 minutes at room temperature, and the resulting intermediate layer buffy coat containing leukocytes was transferred into another centrifugation tube.

Thereafter, total RNAs were obtained in accordance with the AGPC method [*Experimental Medicine*, 9, 1937 (1991)] or using an RNA recovering kit RNAeasy (manufactured by QIAGEN).

(2) Fluorescence differential display using leukocyte total RNAs of IgA nephropathy patients and healthy persons Distilled water was added to 2.5 μg of each of the total RNAs obtained in the above step (1) to a total volume of 9 μl, and the solution was mixed with 1 μl of an anchor primer (50 μM, custom-synthesized by Sawady Technology) whose 5'-end had been fluorescence-labeled with fluorescein isothiocyanate (referred to as "FITC" hereinafter), heated at 70° C. for 5 minute and then immediately cooled on an ice bath.

Since each of the three primers FAH (nucleotide sequence is shown in SEQ ID NO:105), FGH (nucleotide sequence is shown in SEQ ID NO:106) and FCH (nucleotide sequence is shown in SEQ ID NO: 107) was used in each reaction as the 5'-end fluorescence-labeled anchor primer, a total of three combinations of reactions were carried out for one sample of total RNAs.

A 4 μl portion of 5×reverse transcriptase reaction buffer [250 mM tris(hydroxymethyl)aminomethane (Tris)-HCl (pH 8.3), 375 mM KCl, 15 mM MgCl$_2$] was mixed with 2 μl of 100 mM dithiothreitol (DTT), 1 μl of 10 mM dNTP (dATP, dGTP, dTTP and dCTP), 1 μl of distilled water and 1 μl (200 units) of a reverse transcriptase SUPERSCRIPT II RNase H$^-$ Reverse Transcriptase (manufactured by Life Technologies), and the resulting mixture was allowed to stand at room temperature for 10 minutes, allowed to react at 42° C. for 50 minutes to synthesize a cDNA, and then heated at 90° C. for 5 minutes to terminate the reaction.

After the reaction, to the reaction solution was added 40 µl of TE buffer [10 mM Tris-HCl (pH 8.0), 1 mM disodium ethylenediaminetetraacetate (EDTA) (pH 8.0)].

Next, 14.7 µl of distilled water, 2 µl of 10×PCR buffer [100 mM Tris-HCl (pH 8.8), 500 mM KCl, 15 mM $MgCl_2$, 1% Triton X-100], 0.8 µl of 2.5 mM dNTP, 0.3 µl of 50 µM fluorescene-labeled anchor primer (the same among FAH, FGH and FCH used in the cDNA synthesis), 1 µl of 10 µM abitrary primer (manufactured by Operon Technologies) and 0.2 µl of DNA polymerase Gene Taq (5 units/µl, manufactured by Nippon Gene) ware added to 1 µl of each of the thus synthesized cDNA samples, and the resulting mixture was arranged in Thermal Cycler to carry out PCR.

The PCR was effected by carrying out the reaction at 94° C. for 3 minutes, 40° C. for 5 minutes and 72° C. for 5 minutes, subsequently carrying out a total of 27 cycles of the reaction in which one cycle was composed of the steps of 95° C. for 15 seconds, 40° C. for 2 minutes and 72° C. for 1 minute, and finally carrying out 5 minutes of the reaction at 72° C.

Since each reaction was carried out by a combination of one of the above-described three types as the fluorescence-labeled anchor primer with one of 60 types of OPD-1 to 20, OPE-1 to 20 and OPV-1 to 20 manufactured by Operon Technologies as the arbitrary primer, a total of 180 reactions, and since a reaction of the fluorescence-labeled anchor primer FGH with an arbitrary primer OPB-2 (manufactured by Operon Technologies) was also carried out, a total of 181 reactions were carried out for the total RNAs.

A 4 µl portion of each of the PCR reaction solutions was mixed with 3 µl of electrophoresis sample buffer use (95% formamide, 0.1% xylene cyanol, 0.1% Bromophenol Blue), and the mixture was heated at 95° C. for 2 minutes, immediately cooled thereafter on an ice bath and then subjected to 2.5 hours of 6% acrylamide gel electrophoresis at 1,500 V. A solution composed of 89 mM Tris, 89 mM boric acid and 2 mM EDTA was used as the electrophoresis buffer. By measuring fluorescence of the gel after electrophoresis using Fluor Imager (manufactured by Molecular Dynamics), the fragments amplified by PCR were detected and cared. In comparison with 5 cases or the healthy persons, a band which significantly increased or decreased in leukocytes of 5 cases of the IgA nephropathy patients was recorded.

Total RNAs were prepared from other 3 cases of IgA nephropathy patients and 3 cases of healthy persons in the same manner as described in the above step (1) to carry out the differential display of the step (2).

A total of 197 bands which showed increased or decreased fluorescence in both of the above two trials of the differential display were cut off from the gels.

A 38 µl portion of distilled water, 5 µl of 10×PCR buffer, 4 µl of 2.5 mM dNTP, 0.6 µl of an anchor primer (no fluorescence labeling: 34 µM, custom-synthesized by Sawady Technology), 2 µl of 10 µM arbitrary primer and 0.5 µl of DNA polymerase Gene Taq were added to about ¼ portion of each of the gels thus cut off, the resulting mixture was heated at 94° C. for 3 minutes and then a total of 30 cycles of the reaction was carried out in which one cycle was comprised of the steps of 95° C. for 15 seconds, 40° C. for 2 minutes and 72° C. for 1 minute, subsequently carrying out 5 minutes of the reaction at 72° C. to complete PCR.

Each of the resulting reaction solutions was extracted with phenol-chloroform (1:1) and then with chloroform-isoamyl alcohol (24:1), subsequently carrying out ethanol precipitation.

The thus obtained precipitate (amplified DNA fragments) was dissolved in TE buffer and subjected to 1.5% low melting point agarose gel (SEA PLAQUE GTG, manufactured by FMC Bioproducts) electrophoresis.

After the electrophoresis, the resulting gels were stained with ethidium bromide and then the bands containing amplified fragments were cut off.

The gel was heated at 65° C. for 15 minutes to melt agarose and teen extracted with phenol-chloroform and then with chloroform-isoamyl alcohol.

The thus obtained extract was subjected to ethanol precipitation and the resulting precipitate (amplified fragments) was dissolved in 10 µl of TE buffer.

A 1 µl a portion of each of the amplified fragments was mixed with 1 µl of a vector for PCR fragment cloning use, pT7BlueT-Vector (manufactured by Novagen), and the amplified fragment was cloned into the plasmid using DNA Ligation Kit ver.1 (manufactured by Takara Shuzo) in accordance with the manual attached to the kit.

Using the thus obtained recombinant plasmid, *Escherichia coli* DH5α (manufactured by Gibco BRL) was transformed in accordance with a known method, and the resulting transformant was spread on LB agar medium containing 50 µg/ml of ampicillin and cultured overnight at 37° C.

The thus grown ampicillin-resistant transformant was suspended in 20 µl of distilled water, the suspension was mixed with 2.5 µl of 10×PCR buffer, 2 µl of 2.5 mM dNTP, 0.3 µl of 34 µM anchor primer, 1 µl of 10 µM arbitrary primer and 0.5 µl of a DNA polymerase Gene Taq, and the mixture was subjected to PCR under the same conditions of the above-described re-amplification of amplified fragments and then analyzed by electrophoresis which recognized that an amplified fragment has the same length as in the first differential display.

Nucleotide sequence of the amplified fragment was determined using DNA Sequencer (manufactured by Perkin Elmer). In carrying out the nucleotide sequence determination, Dye Primer Cycle Sequencing Kit manufactured by Perkin Elmer and the method described in the manual attached to the kit were used.

Using restriction enzymes capable of cleaving restriction enzyme sites in the determined nucleotide sequence, the reaction product obtained by the above-described differential display was cleaved and then subjected to electrophoresis to recognize that the position of electrophoresis band corresponding to the thus cut off amplified fragment was changed.

Each of the thus obtained nucleotide sequences was compared with a nucleotide sequence data base GenBank to select a total of 66 clones which were not present among the known nucleotide sequences in the data base or coincided only with the expressed sequence tag among nucleotide sequences in the data base.

Example 2

Detection of Specificity of mRNA Expression by RT-PCR

Using 2 µg of each of the total RNAs obtained in Example 1 from leukocytes of five cases of IgA nephropathy patients and 5 cases of healthy persons, a single-stranded cDNA was synthesized using a single-stranded cDNA synthesis kit, Superscript Preamplification System (manufactured by Life Technologies) in accordance with the method described in the manual attached to the kit.

A 21 µl portion of the thus obtained solution containing the single-stranded cDNA was adjusted to a total volume of 420 µl by addis distilled water.

Using 10 µl portion of the thus prepared solution, the expression level of mRNA corresponding to each amplified fragment was detected by carrying out RT-PCR in the following manner.

That is, 10 μl of the leukocyte single-stranded cDNA solution was mixed with 15.8 μl of distilled water, 4 μl of 10×PCR buffer, 3.2 μl of 2.5 mM dNTP, 2 μl of DMSO, 2 μl of 10 μM gene-specific sense primer, 2 μl of 10 μM gene-specific antisense primer and 2 μl of DNA polymerase Gene Taq which had been diluted to 1 unit/μl, and the resulting mixture was heated at 97° C. for 5 minutes, cooled on an ice bath for 5 minutes and then a total of 28 cycles of PCR was carried out in which one cycle was comprised of the steps of 94° C. for 30 seconds, 65° C. for 1 minute and 72° C. for 2 minutes.

After completion of the PCR, 2% agarose gel electrophoresis was carried out, the resulting gel was stained with 0.01% Cyber Green (manufactured by Takara Shuzo), and the amount of the thus stained amplified fragment was determined by Fluor Imager and used as relative expression quantity of mRNA.

In order to make a correction of the amount of mRNA, the same reaction was carried out on a house keeping gene, glyceraldehyde 3-phosphate dehydrogenase (G3PDH) gene, using specific primers (SEQ ID NO:110 and NO: 111) and the expression level of mRNA for each gene was corrected based on the ratio of the expression level of G3PDH mRNA, and then the average value of five cases of IgA nephropathy patients and the average value of 5 cases of healthy persons were compared and 30 gene clones having a difference in their values were selected as genes whose expression quantity was changed in patients with IgA nephropathy. The thus selected genes are summarized in Table 1.

TABLE 1

| No | Gene | Amplification primer[1] | bp[2] | Expression fluctuation[3] | RT-PCR primer[4] | SEQ ID NO.[5] | RT-PCR cycle number |
|---|---|---|---|---|---|---|---|
| 1 | INM063-7 | FGH/OPB-2 | 155 | 12.5 | 43, 44 | 7 | 28 |
| 2 | INP303A | FAH/OPD-5 | 305 | 9.9 | 45, 46 | 39 | 28 |
| 3 | INM315-10 | FAH/OPD-9 | 278 | 2.8 | 47, 48 | 8 | 35 |
| 4 | INP319-3 | FAH/OPD-10 | 135 | 14.4 | 49, 50 | 9 | 28 |
| 5 | INP324A | FAH/OPD-12 | 197 | 19.9 | 51, 52 | 10 | 28 |
| 6 | INP332A | FAH/OPD-16 | 137 | 16.6 | 53, 54 | 11 | 28 |
| 7 | INM335-3 | FAH/OPD-17 | 274 | 4.2 | 55, 56 | 12 | 28 |
| 8 | INM336A | FAH/OPD-17 | 171 | 0.14 | 57, 58 | 13 | 28 |
| 9 | INM351-10 | FCH/OPD-4 | 161 | 1.8 | 59, 60 | 14 | 28 |
| 10 | INP356-4 | FCH/OPD-7 | 323 | 18.5 | 61, 62 | 15 | 35 |
| 11 | INP364A | FCH/OPD-12 | 138 | 3.8 | 63, 64 | 16 | 28 |
| 12 | INP377A | FGH/OPD-1 | 256 | 5.0 | 65, 66 | 40 | 28 |
| 13 | INP379A | FGH/OPD-2 | 244 | 8.6 | 67, 68 | 41 | 35 |
| 14 | INP380A | FGH/OPD-2 | 135 | 15.7 | 69, 70 | 17 | 35 |
| 15 | INP401A | FGH/OPD-20 | 258 | 16.7 | 71, 72 | 42 | 24 |
| 16 | INM403A | FAH/OPE-3 | 219 | 2.3 | 73, 74 | 18 | 28 |
| 17 | INP407A | FAH/OPE-5 | 191 | 9.1 | 75, 76 | 19 | 28 |
| 18 | INM408A | FAH/OPE-5 | 148 | 0.65 | 77, 78 | 20 | 28 |
| 19 | INP410-5 | FAH/OPE-6 | 306 | 2.0 | 79, 80 | 21 | 28 |
| 20 | INM419-14 | FAH/OPE-11 | 357 | 0.064 | 81, 82 | 22 | 35 |
| 21 | INP429A | FGH/OPE-7 | 219 | 2.4 | 83, 84 | 23 | 28 |
| 22 | INP431A | FGH/OPE-8 | 251 | 13.1 | 85, 86 | 24 | 24 |
| 23 | INP438A | FGH/OPE-11 | 233 | 5.4 | 87, 88 | 25 | 24 |
| 24 | INP444A | FGH/OPE-15 | 176 | 3.3 | 89, 90 | 26 | 24 |
| 25 | INP451-2 | FCH/OPE-4 | 241 | 14.0 | 91, 92 | 27 | 32 |
| 26 | INP458A | FCH/OPE-11 | 217 | 9.2 | 93, 94 | 28 | 28 |
| 27 | INP463A | FCH/OPE-19 | 232 | 18.2 | 95, 96 | 29 | 35 |
| 28 | INP470A | FCH/OPV-4 | 228 | 5.8 | 97, 98 | 30 | 28 |
| 29 | INP482A | FCH/OPV-10 | 298 | 9.9 | 99, 100 | 31 | 28 |
| 30 | INP485-6 | FCH/OPV-17 | 291 | 8.5 | 101, 102 | 32 | 28 |

[1]A combination of the anchor primer with the arbitrary primer used in the differential display is shown.
[2]The length of the amplified fragment of the differential display is shown.
[3]Expression fluctuation is shown as the value of "the average value of mRNA expression levels in 5 cases of IgA nephropathy patients/the average value of mRNA expression levels in 5 cases of healthy persons".
[4]The primer used in the RT-PCR is shown by the SEQ ID NO.
[5]SEQ ID NO. of the Sequence Listing corresponding to the nucleotide sequence of amplified fragment obtained by the differential display described in Example 1 is shown.

Thus, it becomes possible to carry out diagnosis of IgA nephropathy by observing the expression levels of these genes in the leukocytes samples to be tested by PT-PCR using primers of these genes and mRNAs of the samples.

Example 3

Cloning of Whole Length cDNA and Analysis of Each cDNA Clone (1) Cloning of whole length cDNA Cloning of a cDNA containing the nucleotide sequence of amplified fragment obtained by differential display was carried out by optionally using gene trapper method, plaque hybridization of a cDNA library and 5'-RACE method. The methods are described below.

(A) Gene trapper method

A cDNA clone was obtained from a human leukocyte cDNA library (manufactured by Life Technologies) by the following method in which pCMV-SPORT (manufactured by Life Technologies) was used as the vector, using GENE TRAPPER cDNA Positive Selection System (manufactured by Life Technologies).

That is, clones in the cDNA library were made into single-stranded DNA (correspond to the antisense strand of cDNA) using Gene II protein and exonuclease III, and hybridization was carried out using a probe, namely a biotinated oligonucleotide specific for each gene (the sense primer specific to each gene, used in the RT-PCR in Example 2, was used).

By allowing the biotinated probe to bind to genetic beads to which streptoavidin had been immobilized, the above-described single-stranded cDNA hybridized with the probe was isolated.

The single-stranded cDNA clone was released from the probe, made into double-stranded DNA using a DNA polymerase and then Escherichia coli was transformed with the double-stranded DNA to obtain a transformant containing the cDNA clone.

Illustrative method employed was as described in the manual attached to the kit.

Each of the thus obtained transformants was suspended in 18 μl of distilled water, the suspension was mixed with 2.5 μl of 10×PCR buffer, 2 μl of 2.5 mM dNTP, 1 μl of 10 μM gene-specific sense primer, 1 µl of 10 µM gene-specific antisense primer and 0.5 µl of DNA polymerase Gene Taq, and the resulting mixture was subjected to PCR under the same conditions as the RT-PCR, subsequently carrying out electrophoresis to isolate a transformant as cDNA clone of interest in which a fragment having a length deduced from the positions of primers was amplified.

(B) Screening of cDNA library

Screening of cDNA clones was carried out by means of plaque hybridization using a cDNA library of leukocytes of patient with IgA nephropathy and a cDNA library of a neuroblastoma cell line NB-1.

Prior to the plaque hybridization of each library, PCR was carried out in the same manner as in Example 2, using each cDNA library as the template and using each of the gene-specific RT-PCR primers used in Example 2, and a library, in which a fragment having a length deduced from the position of the primer was amplified, was selected as the library that contains the cDNA clone of the gene of interest.

Using the library, DNAs in plaques were blotted on a nylon membrane Hybond N+ (manufactured by Amersham).

Using a plasmid which contained the amplified fragment of each gene and was obtained by the differential display of Example 1, as the template, and each of the gene-specific primers used for the RT-PCR in Example 2 as a primer, PCR was carried out by adding PCR DIG labeling mix (manufactured by Boehringer Mannheim) to the reaction solution, thereby amplifying and labeling each gene-specific fragment.

Using each of the thus vilified and labeled gene-specific fragments as a probe, hybridization and detection of positive plaques were carried out in accordance with the manual provided by Boehringer aim.

DIG Nucleic Acid Detection Kit (manufactured by Boehringer Mannheim) was used for the detection.

(B-1) Preparation of IgA nephropathy patient leukocyte cDNA library

A 50 ml portion of blood sample was collected from each of four patients with Ion nephropathy, and each of the blood samples was centrifuged using Polymorphprep to isolate respective leukocyte fractions. The specific method was described in the manual attached to the Polymorphprep.

Using the thus isolated leukocytes, total RNAs were prepared by employing the guanidine thiocyanate-cesium trifluoroacetate method [*Methods in Enzymology*, 154, 3 (1987)]. From a total of 200 ml of blood samples, 320.7 µg of total RNAs was obtained.

A 272.6 µg portion of the thus obtained total RNAs was passed through an oligo(dT) cellulose column to obtain 10.7 µg of mRNA as poly (A)+ mRNA.

In the same manner, 6.9 µg of mRNA was obtained from other four patients of IgA nephropathy.

Using 10.0 µg and 6.4 µg of the thus obtained respective mRNA samples, synthesis of cDNA, addition of EcoRI adapter and digestion reaction with XhoI were carried out using uniZAP-cDNA Synthesis Kit (manufactured by Stratagene), and the resulting fragments were inserted between EcoRI/XhoI of λZap II by ligation to prepare a cDNA library in which the cDNA was invited in such a direction that its 5'-end was always present in the EcoRI site of the vector.

The above specific method was described in the manual provided by Stratagene.

After packaging using a λ phage packaging kit Gigapack III Gold packaging extract (manufactured by Stratagene), *Escherichia coli* XL1-Blue MRF' was infected with the library used as the final cDNA library. The packaging and infection were carried out in accordance with the manual provided by Stratagene.

(B-2) Preparation of neuroblastoma cell line NB-1 cDNA

Using RPMI 1640 medium (manufactured by Nissui Pharmaceutical) containing 10% fetal calf serum (manufactured by Biotech International), 2% penicillin (5,000 units/ml)·streptomycin (5 mg/ml) solution (manufactured by Life Technology), 0.19% NaHCO$_3$ (manufactured by Sigma) and 4 mM glutamine, culturing and subculturing of a neuroblastoma cell line NB-1 (*The Autonomic Nervous System*, 10, 115 (1973), available from Human Science Research Resource Bank as JCRB0621) were carried out at 37° C. in an atmosphere of 5% CO$_2$, and 1.25×10$^8$ of confluent cells wars recovered.

After washing of the thus recovered cells with PBS, 10.2 µg of purified mRNA was obtained using Fast Track mRNA Isolation Kit (manufactured by Invitrogen).

A 6 µg portion of the thus obtained mRNA and 1.5 µg of NotI-primer-adapter (manufactured by Promega) were put into a container, adjusted to 7 µl by adding distilled water, heated at 70° C. for 10 minutes and then rapidly cooled on an ice bath.

The thus rapidly cooled solution was mixed with 4 µl of 5×reverse transcriptase reaction buffer (attached to the enzyme), 2 µl of 100 mM DTT, 1 µl of 10 mM dNTP and 1 µl of [α-$^{32}$P] dCTP (110 TBq/mmol; manufactured by Amersham) as a tracer, and the mixture was incubated at 37° C. for 2 minutes, mixed with 5 µl of (1,000 units) of a reverse transcriptase, SUPERSCRIPT II RNase H$^-$ Reverse Transcriptase, and then allowed to react at 44° C. for 1 hour to synthesize a cDNA.

The thus obtained reaction solution was mixed with 82 µl of distilled water, 32 µl of 5×reaction buffer [100 mM Tris-KCl, 500 mM KCl, 25 mM MgCl$_2$, 50 mM (NH$_4$)$_2$SO$_4$, 10 mM DTT, 250 mg/ml bovine serum albumin (BSA), 750 mM β-nicotinamide dinucleotide], 2.75 µl of 10 mm dNTP, 2.75 µl, of [α-$^{32}$P] dCTP, 5.5 µl of 100 mM DTT, 2.5 µl of 6 units/µl *E. coli* DNA ligase (manufactured by Takara Shuzo), 11.5 µl of 3.5 units/µl *E. coli* DNA polymerase (manufactured by Takara Shuzo) and 2 µl of 0.6 unit/µl of *E. coli* ribonuclease H (manufactured by Takara Shuzo), and the thus prepared mixture was allowed to react at 16° C. for 3 hours to decompose the mRNA and obtain a double-stranded cDNA.

The reaction solution was mixed with 4.8 µl of 1 unit/µl T4 DNA polymerase (manufactured by Takara Shuzo) and subjected to 5 minutes of the reaction at 16° C. to form blunt ends at both termini.

The reaction solution was mixed with 2 µl of 500 mM EDTA (pH 8.0) and 2 µl of 10% sodium dodecyl sulfate (SDS) to terminate the reaction and then extracted with phenolchloroform to denature and remove the enzyme. An aqueous layer was obtained.

In order to remove the cDNA of 400 bp or less in length and unreacted NotI-primer-adapter and nucleotide, the thus obtained aqueous layer was put on SizeSep-400 span column (manufactured by Pharmacia) which had been equilibrated with TE buffer and centrifuged at 400 g for 2 minutes, and the resulting eluate was subjected to ethanol precipitation to recover the cDNA.

The thus recovered cDNA was dissolved by adding 5 µl (50 pmol) of EcoRI adapter (manufactured by Promega) and mixed with 40 µl of the (A) solution of Ligation Kit Ver. 1 (manufactured by Takara Shuzo) and then with 5 µl of the (B) solution, and the resulting mixture was allowed at 15° C. for 2 hours to effect addition of the EcoRI adapter to both termini of the cDNA.

The reaction solution was mixed with 40 µl of 10 mM EDTA (pH 8.0) and heated at 65° C. for 15 minutes to terminate the reaction, and then the cDNA was recovered by ethanol precipitation.

The thus recovered cDNA was dissolved in 36 µl of distilled water and mixed with 5 µl of 10×reaction buffer [500 mM Tris-HCl (pH 7.6), 100 mM MgCl$_2$], 2.5 µl of 100 mM DTT, 2.5 µl of 10 mM ATP and 4 µl of 6 units/µl T4 polynucleotide kinase (manufactured by Takara Shuzo), and the mixture was allowed to react at 37° C. to for 30 minutes to phosphorylate the 5'-end of the added EcoRI adapter.

The reaction solution was mixed with 7.2 µl of distilled water, 1.8 µl of 5M NaCl and 8 units (1 µl) of NotI, and the mixture was subjected to 2 hours of the reaction at 37° C. to cut off the NotI site in the NotI-primer-adapter.

After adding 6 µl of 500 mM EDTA to terminate the reaction, the reaction solution was mixed with 1 µl of 20 µg/µl tRNA and then extracted with phenol-chloroform to denature and remove the enzyme. An aqueous layer was obtained. In order to remove unreacted EcoRI adapter, the thus obtained aqueous layer was put on SizeSep-400 span column which had been equilibrated with TE buffer and centrifuged at 400 g for 2 minutes to recover the eluate.

The thus recovered eluate was overlaid on potassium acetate solution having a concentration gradient of from 5 to 20%, ultracentrifuged at 50,000 rpm for 3 hours and then recovered from the bottom of the centrifugation tube in 21 fractions using a peristaltic pump.

Each of the fractions was subjected to ethanol precipitation to recover cDNA, a portion of each of the thus recovered samples was subjected to agarose gel electrophoresis and then to autoradiography to measure the length of cDNA contained in each fraction, and the samples were recovered in three fractions, namely a fraction (H) containing cDNA of about 3 kb or more, a fraction (M) containing cDNA of 1 to 3 kb and a fraction (L) containing cDNA of 1 kb or less.

A 9 µg (9 µl) portion of a cloning vector ZAP II (manufactured by Stratagene) was mixed with 10 µl of 10×H restriction enzyme buffer (manufacture by Takara Shuzo), 75 µl of distilled water and 90 units (6 µl) of EcoRI, and the mixture was subjected to 2 hours of the reaction at 37° C.

The reaction solution was mixed with 1 µl of 5M NaCl and 40 units (5 µl) of NotI, allowed to react at 37° C. for 2 hours, and further mixed with 8 units (1 µl) of NotI and again subjected to 1 hour of the reaction at 37° C. to cleave the EcoRI site and NotI site of the vector.

The reaction solution was mixed with 100 µl of 2M Tris-HCl (pH 8.0) and 1 unit (2 µl) of E. coli C75 alkaline phosphatase (manufactured by Takara Shuzo) and allowed to react at 60° C. for 30 minutes to dephosphorylate the 5'-ends cleaved by EcoRI and NotI the vector, and then these enzymes were removed by repeating phenol-chloroform extraction twice.

After removal of the enzymes, chloroform extraction was carried out and the resulting water layer was subjected to ethanol precipitation to recover the vector DNA which was subsequently dissolved in TE buffer.

Each of the cDNA samples recovered in three fractions was mixed with 1 µg of the vector DNA and subjected to ethanol precipitation, and the thus recovered vector DNA and cDNA were dissolved in 4 µl of a ligase buffer [100 mM Tris-HCl (pH 7.6), 5 mM MgCl$_2$, 300 mM NaCl], mixed with 4 µl of the (B) solution of Ligation Kit Ver.1 and then allowed to react at 26° C. for 10 minutes to bind the cDNA to the vector DNA.

A 4 µl portion of each of the reaction solutions was subjected to packaging using a λ phage packaging kit, Giga-Pack Gold II (manufactured by Stratagene). The reagents and methods were described in the manual attached to the kit.

E. coli XL1-Blue HRF' was infected with the thus obtained phage and the titer was measured. Thereafter, the cDNA library was amplified once by growing the phage on a plate medium and recovering it in SM buffer and used as the final cDNA library. The measurement of titer and amplification of library were carried out in accordance with the manual attached to the λ phage packaging kit. A library prepared from the (9) fraction containing cDNA of about 3 kb or more was used for the screening of the present invention.

(C) 5'-RACE

5'-RACE of the IgA nephropathy patient cDNA prepared in the above method (B) was carried out using 5'-RACE System ver.2 (manufactured by Life Technologies). The specific method was described in the manual attached to the kit.

Using the above methods (A) to (C), cDNA cloning of the five genes shown in Table 2 was achieved.

TABLE 2

| Gene name | SEQ ID NO. | cDNA clone | Method[1] | cDNA source |
|---|---|---|---|---|
| INP303A | 1 | GTINP303A-41a | A | human leukocytes |
| | | INP303A ph1-3 | B | NB-1 |
| | | INP303A-R1 | C | IgA nephropathy leukocytes |
| INP377A | 2 | GTINP377A-46C | A | human leukocytes |
| INP379A | 3 | PHINP379A-16-2 | B | IgA nephropathy leukocytes |
| INP401A | 4 | PHINP401A-8-1 | B | IgA nephropathy leukocytes |
| | 5 | PHINP401A-14-1 | B | IgA nephropathy leukocytes |
| GTINP332A-21 | 6 | GTINP332A-21 | A | human leukocytes |
| | | PHDTINP332A-21-28-1 | B | IgA nephropathy leukocytes |

[1]Cloning method of each cDNA clone obtained:
A: gene trapper method,
B: plaque hybridization of cDNA library
C: 5'-RACE method.

Nucleotide sequence of the cDNA moiety of each of the thus obtained cDNA clones was determined using 377 DNA Sequencer manufactured by Perkin Elmer. Determination of the nucleotide sequence was carried out using Dye cycle sequencing FS Ready Reaction Kit in accordance with the manual attached to the kit. Additionally, the nucleotide sequence was translated into amino acid sequence by three frames to examine whether an open reading frame (ORF) composed of 100 or more amino acids is present.

(1) INP303A

A cDNA clone GTINP303A-41a was obtained by the gene trapper method, but this was considered to be an incomplete cDNA clone because of the absence of ORF, which corresponds to 100 or more amino acids, in the nucleotide sequence of the cDNA.

In order to obtain a full-length length cDNA clone, 5'-RACE was carried out using specific primers (nucleotide sequences are shown in SEQ ID NO:108 and NO:109) which correspond to a moiety close to the 5'-end of GTINP303A-41a to obtain cDNA clone INP303A-R1. Also, since a part of the cDNA nucleotide sequence of GTINP303A-41a was not able to determine, another cDNA clone INP303A-ph1–3 was obtained from an NB-1 cDNA library by plaque hybridization.

By combining nucleotide sequences of these cDNA clones thus obtained, a 4,276 bp nucleotide sequence of the cDNA of INP303A was determined as shown in SEQ ID No:1.

The nucleotide sequence of a fragment obtained by differential display (SEQ ID NO:39) coincided with the complementary chain nucleotide sequence corresponding to the positions 2,797 to 3,101 of SEQ ID NO:1. Therefore, it was considered that the anchor primer was not annealed to the 3'-end poly (A) sequence of mRNA but to the complementary chain of a sequence having a series of T and existing in the positions 2,782 to 2,795 of SEQ ID NO:1.

An ORF corresponding to 239 amino acids (corresponds to the positions 53 to 742 of SEQ ID NO: 1, the amino acid sequence is shown in SEQ ID NO:33) was found in the nucleotide sequence of the of INP303A-R1.

When the amino acid sequence of the ORF was compared with an amino acid data base, it was found that this sequence has a homology with C40H1 which was estimated to be a protein encoded by a Nematoda genomic gene clone C40H1, mouse cytoplasmic polyadenylation element binding protein (CPEBP) and Drosophila orb gene.

It was found also that an amino acid sequence just downstream of the region where these proteins showed a homology with the INP303A protein also showed a homology with the amino acid sequence encoded by the nucleotide sequence of positions 3,346 to 3,577 of SEQ ID NO:1. Therefore, it was assumed that this cDNA is a result of abnormal splicing in which a 2,689 bp nucleotide sequence (corresponds to positions 713 to 3,352 in SEQ ID NO:1) which seems to be an intron originally nod in the nucleotide sequence of INP303A.

It was found that the nucleotide sequence of a fragment which was obtained by the differential display and whose expression quantity increased in IgA nephropathy patients is present in this insertion sequence and the amount of mRNA which caused such an abnormal splicing increases in IgA nephropathy patients. It is highly possible that a protein translated from an mRNA which caused the abnormal splicing does not exert its original function, because its amino acid sequence at and after the 220 position is different from the original protein encoded by INP303A, namely a protein (295 amino acids) encoded by a nucleotide sequence resulting from the elimination of intron deduced from the a homology.

(2) INP377A

Nucleotide sequence of the cDNA of cDNA clone GTINP377A-46C was determined by the gene trapper method, with the thus obtained nucleotide sequence shown in SEQ ID NO:2.

When the nucleotide sequence of INP377A cDNA was compared with a nucleotide sequence data base, it was found that a sequence of the positions 1 to 552 of a human gene LUCA15 (GenBank accession No. U23946) which has a homology with a Drosophila cancer inhibition gene S×1 coincides with the 50 to 527 position nucleotide sequence and 1,010 to 1,083 position nucleotide sequence of GTINP377A-46C. Consequently, it was assumed that GTINP377A-46C in a cDNA clone in which an intron of LUCA15 remained by an abnormal splicing.

A nucleotide sequence (SEQ ID NO:40) of a fragment obtained by the differential display method coincided with the nucleotide sequence of a complementary chain corresponding to the positions 759 to 1,014 of SEQ ID NO:2. Accordingly, it was considered that the anchor primer was not annealed to the 3'-end poly (A) sequence of mRNA but to the complementary chain of a sequence having a series of T and existing in the positions 745 to 757 of SEQ ID NO:2. Since the nucleotide sequence of the fragment is considered to be present in the nucleotide sequence which seems to be an intron of LUCA15, it is probable that the amount of mRNA which caused such an abnormal splicing increases in IgA nephropathy patients.

It is highly possible that the protein of 143 amino acids (the amino acid sequence is shown in SEQ ID NO: 34) which is encoded by GTINP377A-46C does not exert its original function, because its amino acid sequence at and after the 137 position is different from the original protein (815 amino acids) encoded by LUCA15 cDNA.

(3) INP379A

A DNA clone of INP379A, namely PHINP379A-16-2, was obtained by plaque hybridization of a cDNA library prepared from leukocytes of IgA nephropathy patients.

When the nucleotide sequence of the cDNA was determined, the XhoI site and poly T sequence were present in a side which was thought to be the 5'-end, so that it was considered that this is a clone in which cDNA was inserted into the vector in the opposite direction.

Consequently, a nucleotide sequence complementary to the thus obtained nucleotide seqyenc, which is the original nucleotide sequence of the cDNA, is shown in SEQ ID NO:3.

The nucleotide sequence of a fragment obtained by differential display (SEQ ID NO:41) coincided with the nucleotide sequence of the positions 2,706 to 2,949 of SEQ ID NO:3. An ORF corresponding to 104 amino acids (the amino acid sequence is shown in SEQ ID NO:35) was present in this nucleotide sequence.

Since no sequences having a homology with this amino acid sequence were found in the amino acid sequence data base, this cDNA was considered to be a gene which encodes a novel protein.

(4) INP401A

Two cDNA clones of INP401A, namely PHINP401A-8-1 and PHINP401A-14-1, were obtained by plaque hybridization of a cDNA library prepared from leukocytes of IgA nephropathy patients.

When nucleotide sequences of both cDNAs were determined, it was found that both sequences contained the same ORF corresponding to 133 amino acids, except for only one different base and tore only one corresponding amino acid. Also, since both sequences are different from each other with regard to their nucleotide sequences of 5'-side non-translation region and 3'-side non-translation region, the presence of mRNAs having different polymorphism and splicing of the gene was assumed.

The nucleotide sequence of PHINP401A-8-1 is shown in SEQ ID NO:4, the nucleotide sequence of PHINP401A-14-1 in SEQ ID NO:5, the amino acid sequence of the protein encoded by PHINP401A-8-1 is shown in SEQ ID NO:36, and the amino acid sequence of the protein encoded by PHINP401A-14-1 in SEQ ID NO:37.

The nucleotide sequence of a fragment obtained by differential display (SEQ ID NO: 42) coincided with the complementary chain nucleotide sequence corresponding to the positions 960 to 1,217 of SEQ ID NO: 4 and the complementary chain nucleotide sequence corresponding to the positions 1,313 to 1,570 of SEQ ID NO:5. Accordingly, it was considered that the anchor primer was not annealed to the 3'-end poly (A) sequence of mRNA but to the complementary chain of a sequence having a series of T and existing in the positions 947 to 959 of SEQ ID NO:4 or the positions 1,302 to 1312 of SEQ ID NO:5.

The nucleotide sequence of a fragment which was obtained by the differential display and whose expression quantity increased in IgA nephropathy patients was found to have a nucleotide sequence complementary to the nucleotide sequences of PHINP40A-B-1 and PHINP401A-14-1.

The homology of the proteins encoded by PHINP401A-B-1 and PHINP401A-14-1 was examined, but no sequences having a homology were found in the amino acid sequences data base. Accordingly, they were considered to encode novel proteins.

An analysis of hydrophilic property deduced from the amino acid sequence showed a possibility that the protein amino by INP401A is a secretory protein, and, in that case, the 1 to 15 position amino acid sequence of SEQ ID NO:36 or NO:37 was assumed to the signal peptide.

(5) GTINP322A-21

An attempt was made to obtain a cDNA clone of INP332A by the gene trapper method; however, nucleotide sequence of the thus obtained cDNA clone GTINP322A-21 contained no nucleotide sequence which coincides with the amplified differential display fragment of INP332A. Accordingly, this was considered to be a cDNA clone of other gene.

With regard to GTINP332A-21, when the expression quantity of the gene in leukocytes of IgA nephropathy patients and healthy persons was examined by the RT-PCR method described in Example 2 using primers (SEQ ID NO: 103 and NO:104) prepared based on the nucleotide sequence, 4.6 times higher increase in the expression quantity was found in the IgA nephropathy patients in comparison with the case of healthy persons.

Using the cDNA moiety of GTINP322A-21 as a probe, a cDNA clone PHGTINP332A-21-28-1 was obtained by plaque hybridization of the cDNA library of IgA nephropathy patient leukocytes.

Determination of the cDNA nucleotide sequence of the clone revealed the presence of an ORF corresponding to 128 amino acids. The cDNA nucleotide sequence of PHGTINP332A-21-28-1 is shown in SEQ ID NO:6, and the amino acid sequence of the protein encoded by the ORF is shown in SEQ ID NO:38.

It was found that the amino acid sequence of the ORF has a homology with the SH2 domain of, for example, phosphatidylinositol 3,4,5-triphospho-5-phosphatase, which has a function to bind to phosphorylated tyrosine.

As clear from the above examples, the diagnosis, treatment or prevention of IgA nephropathy can be effected using the DNA, protein and antibody of the present invention.

While the invention has bee described in detail and with reference to specific embodiments thereof, it will be apparent to one skilled in the art that various changes and modifications can be made therein without departing from the spirit and scope thereof.

What is claimed is:

1. An isolated DNA comprising a nucleotide sequence selected from the group of nucleotide sequences consisting of SEQ ID NOS:1–6 and 9–12.

2. A composition comprising the DNA according to claim 1 and a diagnostic acceptable carrier.

3. A composition comprising the DNA according to claim 1 and a pharmaceutical acceptable carrier.

4. A method for detecting a mRNA which comprises a nucleotide sequence selected from the group of nucleotide sequences consisting of SEQ ID NO S:1–6 and 9–12 by RT-PCR, comprising:
   (a) isolating a total RNA from a sample;
   (b) synthesizing a cDNA from the RNA; and
   (c) amplifying and detecting a DNA fragment by PCR using (i) a DNA comprising a nucleotide sequence identical to any continuous 10 to 50 residues of a nucleotide sequence selected from the group of nucleotide sequences consisting of SEQ ID NOS:1–6 and 9–12 and (ii) a DNA comprising a nucleotide sequence identical to any continuous 10 to 50 residues of a complementary sequence of the nucleotide sequence selected from the group of nucleotide sequence consisting of SEQ ID NOS: 1–6 AND 9–12 in (i) as primers and the cDNA as a template.

5. A method for diagnosing IgA nephropathy in a subject comprising:
   (a) detecting mRNA comprising a nucleotide sequence elected from the group of nucleotide sequences consisting of SEQ ID NOS:1∝6 and 9–12 in leukocytes of a subject and healthy person; and
   (b) diagnosing IgA nephropathy in the subject based on increased level of said mRNA in leukocytes of the subject as compared with those of healthy persons.

* * * * *

UNITED STATES PATENT AND TRADEMARK OFFICE
CERTIFICATE OF CORRECTION

PATENT NO. : 6,828,428 B2
DATED : December 7, 2004
INVENTOR(S) : Tetsuyoshi Ishiwata et al.

It is certified that error appears in the above-identified patent and that said Letters Patent is hereby corrected as shown below:

<u>Title page</u>,
Item [56], References Cited, FOREIGN PATENT DOCUMENTS,
"DK    4238778 A  *        11/1992" should read
-- DE    4238778 A  *        11/1992 --.
OTHER PUBLICATIONS,
"Alberts, et al." reference, "Biologoy" should read -- Biology --.
"Kidny International," reference, "Kidny" should read -- Kidney --.

<u>Column 1</u>,
Line 15, "DNA" should read -- DNA, --.

<u>Column 3</u>,
Line 4, "NO:1 to" (first occurrence) should be deleted.

<u>Column 4</u>,
Line 11, "(1992)," should read -- (1982), --;
Line 13, "(1925)," should read -- (1985), --; and
Line 30, "brow." should read -- below. --.

<u>Column 6</u>,
Line 12, "3," should read -- 38, --.

<u>Column 7</u>,
Line 52, "(manufacture" should read -- (manufactured --.

<u>Column 8</u>,
Line 41, "16," should read -- 168, --.

<u>Column 9</u>,
Line 7, "cytomagalovirus" should read -- cytomegolovirus --;
Line 12, "call" should read -- cell --;
Line 25, "Unowned" should read -- Unexamined --; and
Line 60, "or a" should read -- or an --.

<u>Column 10</u>,
Line 4, "an" should read -- a --;
Line 50, "by" should read -- be --; and
Line 56, "call" should read -- cell --.

UNITED STATES PATENT AND TRADEMARK OFFICE
CERTIFICATE OF CORRECTION

PATENT NO. : 6,828,428 B2
DATED : December 7, 2004
INVENTOR(S) : Tetsuyoshi Ishiwata et al.

It is certified that error appears in the above-identified patent and that said Letters Patent is hereby corrected as shown below:

Column 12,
Line 36, "shows" should read -- show --;
Line 44, "hybrid a," should read -- hybridoma, --;
Line 55, "256," should read -- 276, --;
Line 57, "5," should read -- 256, --;
Line 59, "call" should read -- cell --; and
Line 60, "calls" should read -- cells --.

Column 13,
Line 48, "ant" should read -- antibody --.

Column 14,
Line 49, "minute" should read -- minutes --.

Column 15,
Line 12, "ware" should read -- were --.

Column 16,
Line 65, "addis" should read -- adding --.

Column 19,
Line 30, "vilified" should read -- amplified --; and
Line 50, "$(A)^+$ mRNA." should read -- $(A)^+$ RNA. --.

Column 20,
Line 34, "Tris-KCl," should read -- Tris-HCl, --; and
Line 37, "2.75 $\mu$l," should read -- 2.75 $\mu$l --.

Column 22,
Line 34, "(9)" should read -- (H) --.

Column 24,
Line 45, "seqyenc," should read -- sequence, --.

Column 99,
Line 32, "NO S:1-6" should read -- NOS:1-6 --.

UNITED STATES PATENT AND TRADEMARK OFFICE
CERTIFICATE OF CORRECTION

PATENT NO.     : 6,828,428 B2
DATED          : December 7, 2004
INVENTOR(S)    : Tetsuyoshi Ishiwata et al.

It is certified that error appears in the above-identified patent and that said Letters Patent is hereby corrected as shown below:

<u>Column 100</u>,
Line 27, "AND" should read -- and --;
Line 33, "1∝6" should read -- 1-6 --; and
Line 35, "on" should read -- on an --.

Signed and Sealed this

Eighteenth Day of October, 2005

JON W. DUDAS
*Director of the United States Patent and Trademark Office*